(12) United States Patent
Gause et al.

(10) Patent No.: US 7,862,597 B2
(45) Date of Patent: Jan. 4, 2011

(54) SYSTEM FOR STABILIZING A PORTION OF THE SPINE

(75) Inventors: Larry Gause, Memphis, TN (US); Dusty Anna Needham, Eads, TN (US); Robert Weakley, Collierville, TN (US); Kenneth S. Shipp, Collierville, TN (US); Benjamin Garden, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 981 days.

(21) Appl. No.: 10/603,471

(22) Filed: Jun. 25, 2003

(65) Prior Publication Data

US 2004/0039387 A1 Feb. 26, 2004

Related U.S. Application Data

(60) Provisional application No. 60/405,360, filed on Aug. 22, 2002, provisional application No. 60/422,298, filed on Oct. 30, 2002.

(51) Int. Cl.
*A61B 17/80* (2006.01)

(52) U.S. Cl. ..................................................... 606/290

(58) Field of Classification Search ............. 606/69–73, 606/60, 61
See application file for complete search history.

(56) References Cited

U.S. PATENT DOCUMENTS

| | | | |
|---|---|---|---|
| 2,977,150 A | 5/1957 | Thomas | |
| 3,741,205 A | 6/1973 | Markolf et al. | |
| 3,814,102 A | 6/1974 | Thal | |
| 4,401,112 A | 8/1983 | Rezaian | |
| 4,834,090 A | 5/1989 | Moore | |
| 5,261,910 A | 11/1993 | Warden et al. | |
| 5,324,290 A | 6/1994 | Zdeblick et al. | |
| 5,344,421 A | 9/1994 | Crook | |
| 5,364,399 A | 11/1994 | Lowery et al. | |
| 5,391,181 A | 2/1995 | Johnson et al. | |
| 5,423,826 A | 6/1995 | Coates et al. | |
| 5,423,854 A | 6/1995 | Martin et al. | |
| 5,431,652 A | 7/1995 | Shimamoto et al. | |
| 5,501,685 A | 3/1996 | Spetzler | |
| 5,616,144 A | 4/1997 | Yapp et al. | |
| 5,676,666 A | 10/1997 | Oxland et al. | |
| 5,681,311 A | 10/1997 | Foley et al. | |
| 5,755,721 A | 5/1998 | Hearn | |

(Continued)

FOREIGN PATENT DOCUMENTS

CA 2201464 10/1998

(Continued)

OTHER PUBLICATIONS

Osteosynthesis Traumatology Orthopaedics; Nov. 1996, Osteo AG, Selzach, Switzerland; 222910; XP-002278234; p. 3.06 "Repositioning and Plate Holding Forceps."

*Primary Examiner*—Anu Ramana

(57) ABSTRACT

A system for stabilizing a portion of the spine comprising an elongate plate attached to one or more vertebrae by a number of bone anchors, with the system including one or more features that provide visualization of an implant disposed within a vertebral space and/or the interface between the implant and the adjacent vertebral tissue. A holding instrument is included that is engageable to the plate for positioning the plate adjacent the spinal column.

40 Claims, 14 Drawing Sheets

U.S. PATENT DOCUMENTS

| | | | |
|---|---|---|---|
| 5,851,207 A | 12/1998 | Cesarone | |
| 5,904,683 A | 5/1999 | Pohndorf et al. | |
| 5,954,722 A | 9/1999 | Bono | |
| 6,017,345 A | 1/2000 | Richelsoph | |
| 6,066,142 A | 5/2000 | Serbousek et al. | |
| 6,129,730 A * | 10/2000 | Bono et al. | 606/73 |
| 6,139,550 A | 10/2000 | Michelson | |
| 6,152,927 A | 11/2000 | Farris et al. | |
| 6,193,721 B1 * | 2/2001 | Michelson | 606/70 |
| 6,228,085 B1 | 5/2001 | Theken et al. | |
| D449,692 S | 10/2001 | Michelson | |
| 6,306,139 B1 * | 10/2001 | Fuentes | 606/70 |
| 6,342,055 B1 | 1/2002 | Eisermann et al. | |
| 6,342,057 B1 * | 1/2002 | Brace et al. | 606/96 |
| 6,379,364 B1 | 4/2002 | Brace et al. | |
| 6,413,259 B1 | 7/2002 | Lyons et al. | |
| 6,454,771 B1 | 9/2002 | Michelson | |
| 6,458,133 B1 | 10/2002 | Lin | |
| 6,503,250 B2 * | 1/2003 | Paul | 606/69 |
| 6,514,274 B1 * | 2/2003 | Boucher et al. | 606/232 |
| 6,533,786 B1 * | 3/2003 | Needham et al. | 606/61 |
| 6,602,255 B1 * | 8/2003 | Campbell et al. | 606/69 |
| 6,660,006 B2 * | 12/2003 | Markworth et al. | 606/61 |
| 6,666,870 B2 * | 12/2003 | Dixon et al. | 606/76 |
| 6,793,658 B2 * | 9/2004 | LeHuec et al. | 606/61 |
| 7,011,665 B2 * | 3/2006 | Null et al. | 606/99 |
| 2002/0077630 A1 | 6/2002 | Lin | |
| 2002/0151899 A1 | 10/2002 | Bailey et al. | |
| 2003/0105462 A1 | 6/2003 | Haider | |

FOREIGN PATENT DOCUMENTS

| | | |
|---|---|---|
| DE | 1 566 110 | 4/1970 |
| DE | 296 20 086 U1 | 1/1997 |
| DE | 199 14 387 A1 | 3/1999 |
| DE | 201 10 393 U1 | 8/2001 |
| EP | 0 637 437 A1 | 2/1995 |
| EP | 0 897 697 A1 | 2/1999 |
| WO | WO 96/05778 | 2/1996 |
| WO | WO 99/04718 | 2/1999 |
| WO | WO 00/59388 | 10/2000 |
| WO | WO 02/09607 A1 | 2/2002 |
| WO | WO 02/24120 A1 | 3/2002 |

* cited by examiner

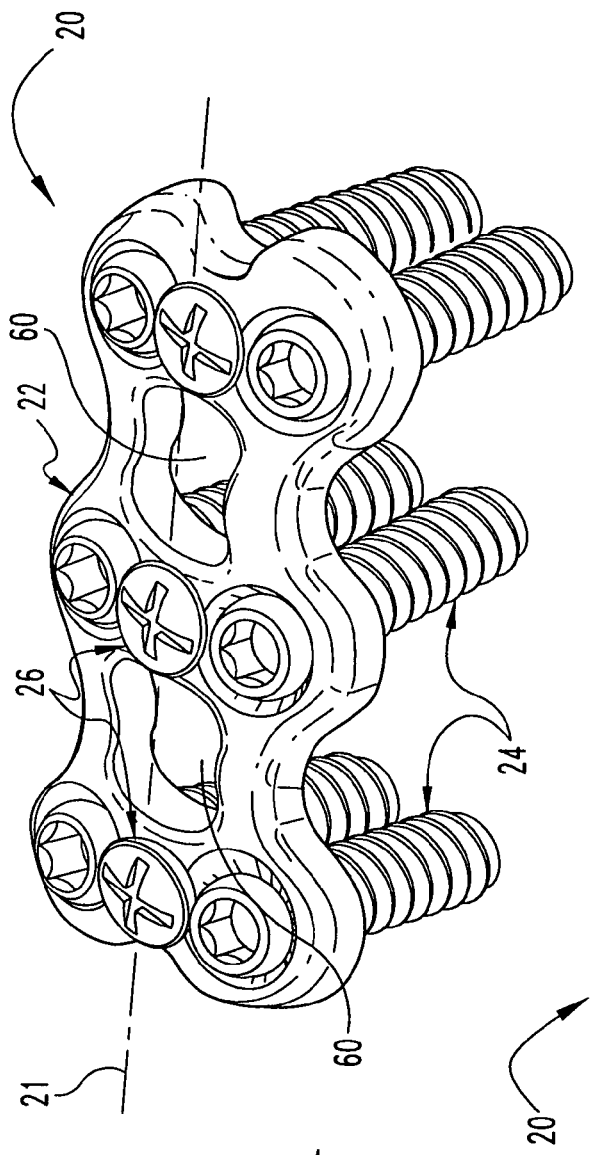
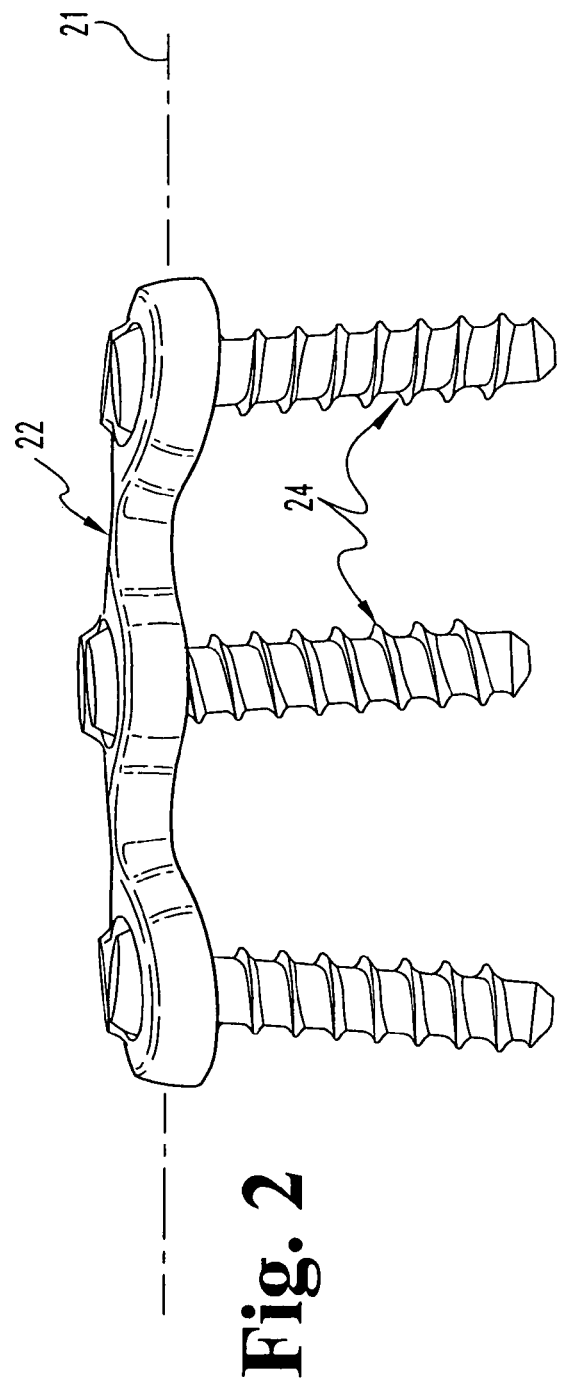
Fig. 1
Fig. 2

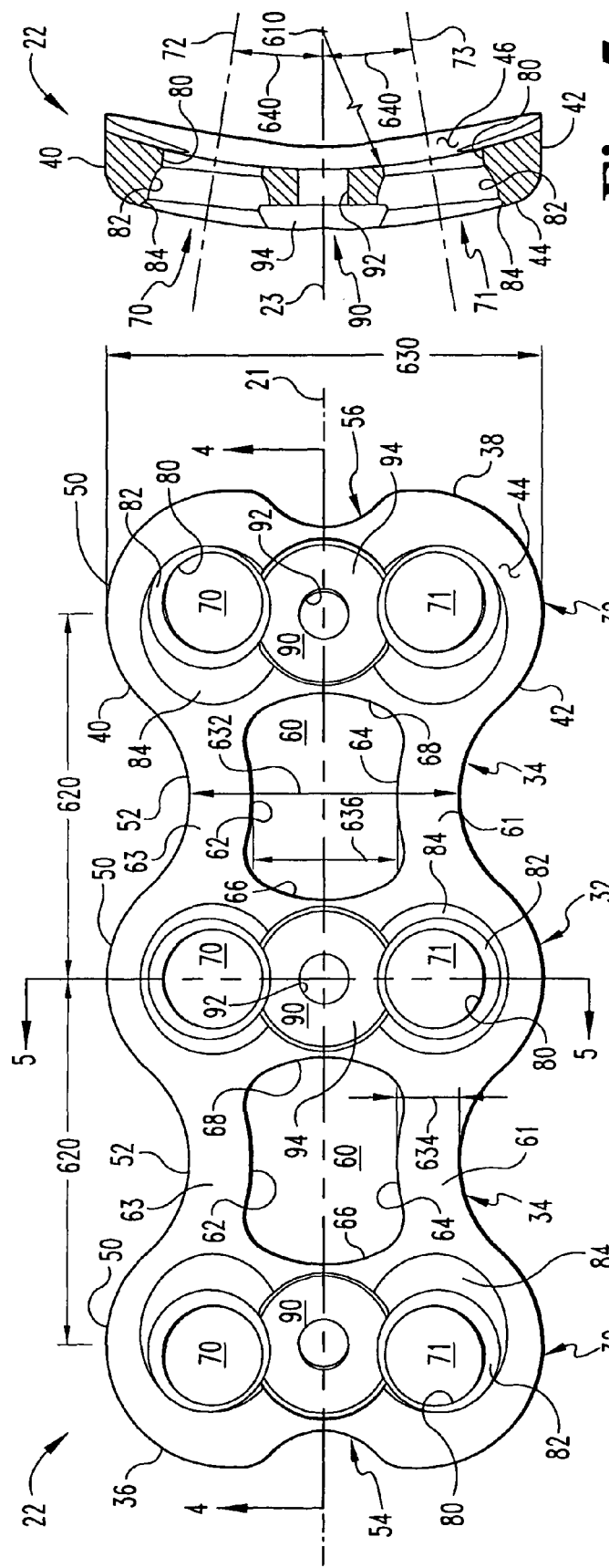
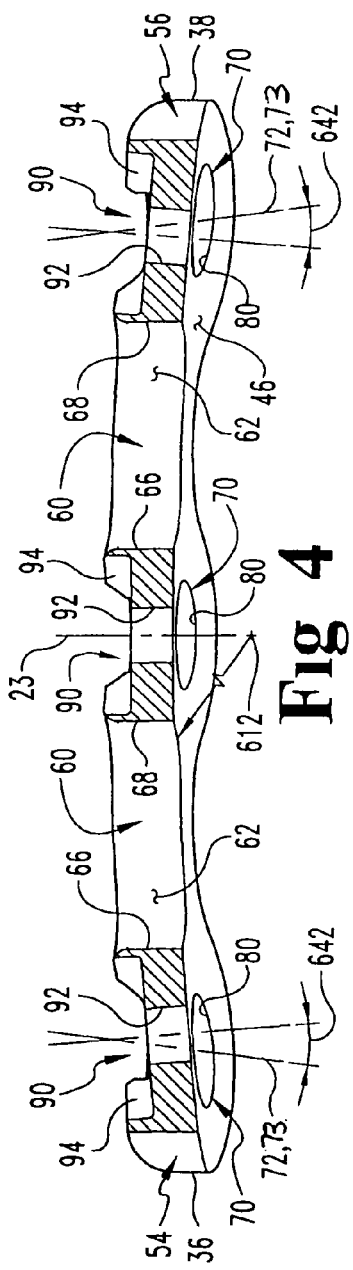
Fig. 3
Fig 4
Fig 5

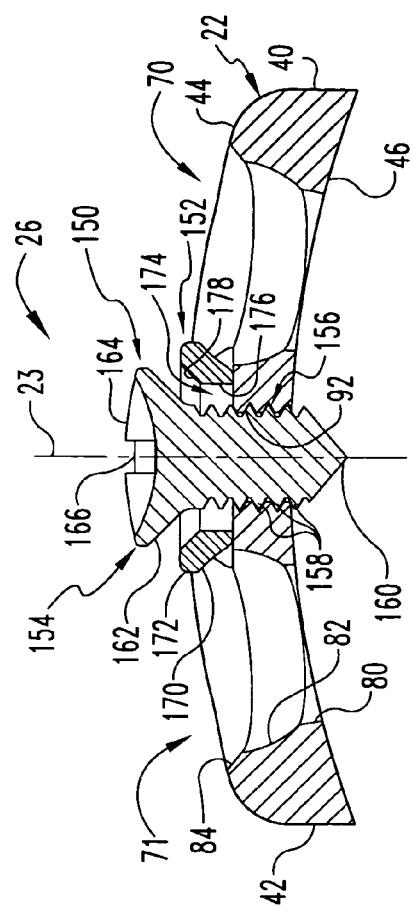

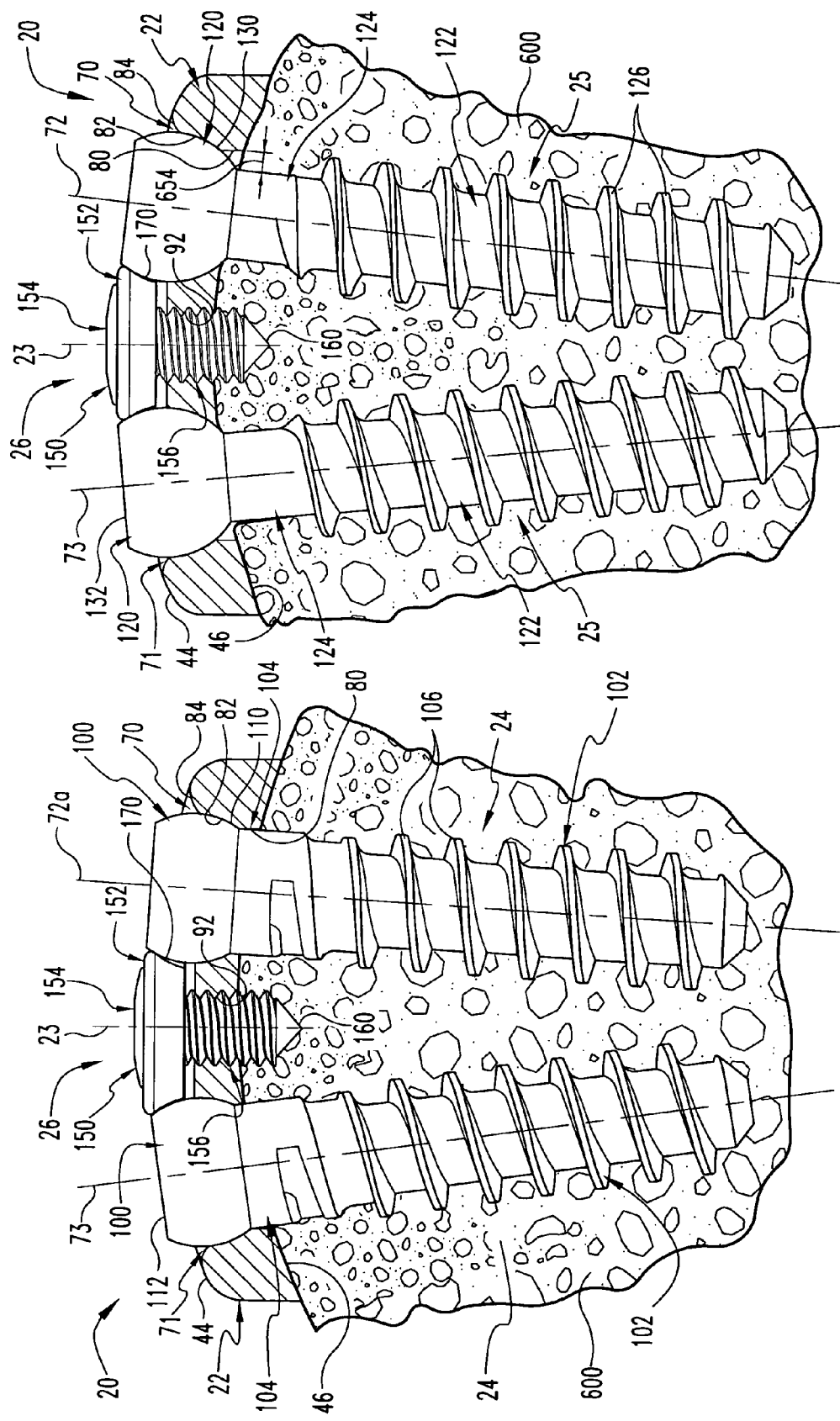

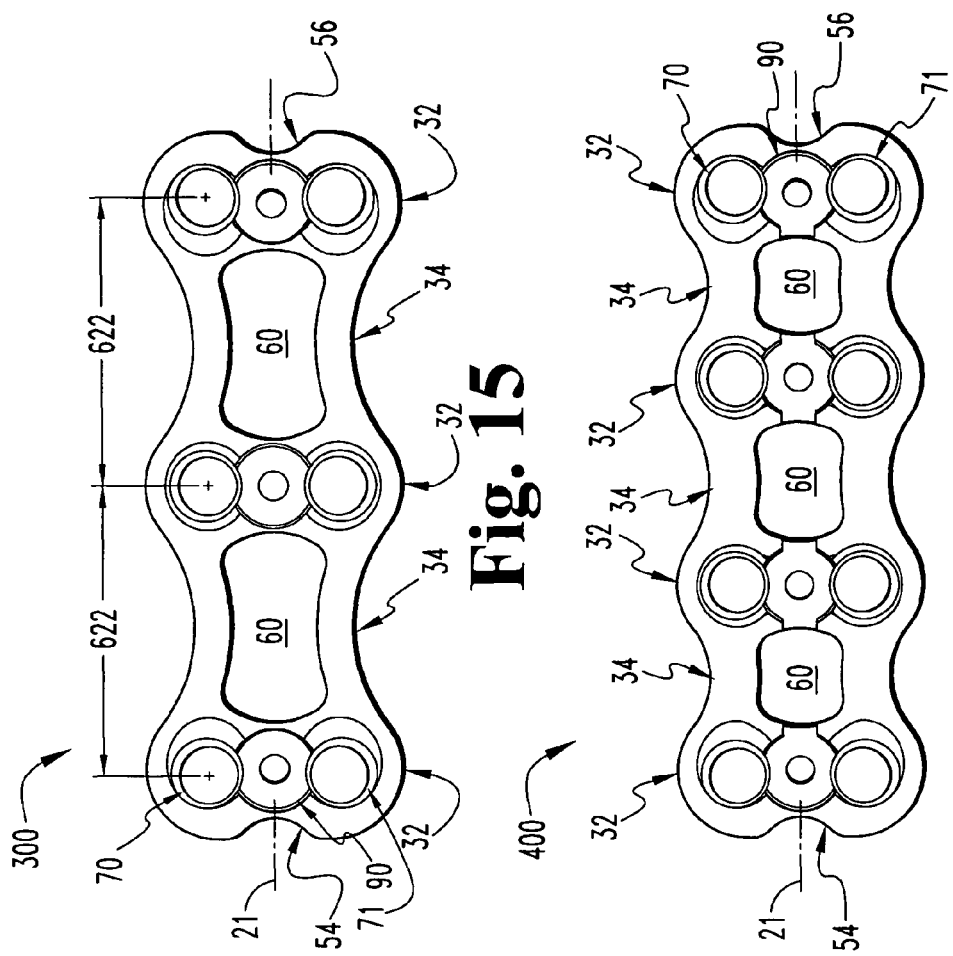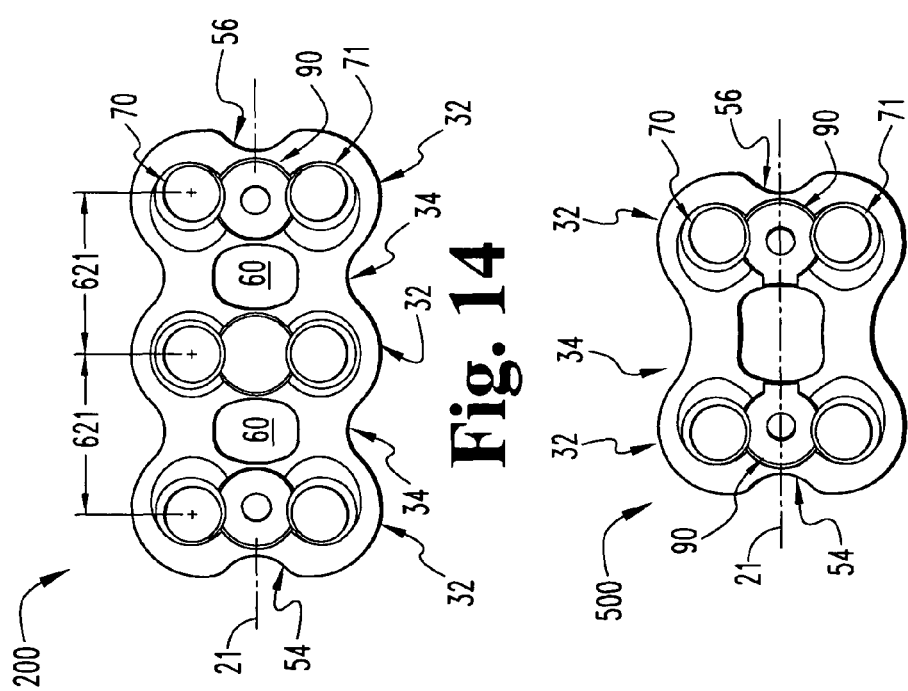

SYSTEM FOR STABILIZING A PORTION OF THE SPINE

CROSS REFERENCE TO RELATED APPLICATIONS

The present application claims the benefit of the filing dates of U.S. Provisional Application Ser. No. 60/405,360, filed on Aug. 22, 2002, and U.S. Provisional Application Ser. No. 60/422,298 filed on Oct. 30, 2002, the contents of each of which are hereby incorporated by reference in their entirety.

BACKGROUND

The invention generally relates to systems for treatment of the spine, and more particularly to systems for stabilizing a portion of the spine for the treatment of various spinal pathologies.

While attempts have been made to develop spinal stabilization systems that address some of the needs and requirements for stabilization and/or fixation of the spine, there still remains a need for improved systems and methods. For example, stabilization systems and methods sometimes utilize an interbody fusion device, such as a bone graft, which is inserted within the intervertebral disc space between adjacent vertebrae to promote bony fusion. An elongate plate is typically attached to the vertebrae to provide temporary stabilization during the fusion process.

Placement and attachment of the elongate plate to the spine can be hindered since the plate and/or the instruments provided for placement and attachment can obscure visualization of the surgical site once the plate is positioned adjacent the vertebrae. As a result, verification of placement of the plate and/or the interbody fusion device requires additional x-rays or utilization of other radiographic imaging techniques. The present invention attempts to eliminate or minimize these verification requirements, to provide the surgeon with added confidence regarding proper placement of the plate and/or the interbody fusion device, to reduce the time required to place the plate and/or the interbody fusion device, and/or to minimize the patient's exposure to radiation.

Thus, there is a general need in the industry to provide improved systems for stabilizing a portion of the spine.

SUMMARY

The present invention relates generally to a system for stabilizing a portion of the spine. Certain forms of the invention that are characteristic of the embodiments disclosed herein are described briefly as follows.

A system for stabilizing a portion of the spine is provided, comprising an elongate plate attached to one or more vertebrae by a number of bone anchors, with the system including one or more features that provide visualization of an implant disposed within a vertebral space and/or the interface between the implant and adjacent vertebral tissue.

In one aspect, the visualization feature comprises at least one visualization opening formed through the elongate plate.

In another aspect, the visualization feature comprises providing at least one portion of the elongate plate with a reduced lateral profile.

In another aspect, the visualization feature comprises forming at least a portion of the elongate plate from a translucent material.

In another aspect, the visualization feature comprises forming at least a portion of the elongate plate from a radiolucent material.

In another aspect, the visualization feature comprises forming the elongate plate from a plurality of modular components.

In another aspect, the visualization feature comprises providing a method of attaching the elongate plate to the vertebrae which minimizes interference with visualization of the implant and/or the interface between the implant and adjacent vertebral tissue.

In another aspect, the visualization feature comprises instrumentation for attaching the elongate plate to the vertebrae which minimizes interference with visualization of the implant and/or the interface between the implant and adjacent vertebral tissue.

Further objects, features, advantages, benefits, and further aspects of the present invention will be apparent from the drawings and description contained herein.

BRIEF DESCRIPTION OF THE FIGURES

FIG. 1 is a perspective view of a spinal stabilization system.

FIG. 2 is a side elevational view of the spinal stabilization system shown in FIG. 1.

FIG. 3 is a top plan view of one embodiment of an elongate plate for use in association with the spinal stabilization system shown in FIG. 1.

FIG. 4 is a cross-sectional view of the elongate plate shown in FIG. 3, as viewed along line 4-4 of FIG. 3.

FIG. 5 is a cross-sectional view of the elongate plate shown in FIG. 3, as viewed along line 5-5 of FIG. 3.

FIG. 9 is an exploded partial side elevational view of one embodiment of a retaining device for use in association with the spinal stabilization system shown in FIG. 1.

FIG. 10 is a cross-sectional view of the retaining device shown in FIG. 9 partially secured to the plate, as viewed along line 10-10 of FIG. 9.

FIG. 11 is a partial cross-sectional view of the spinal stabilization system shown in FIG. 1, as engaged to a vertebra using the fixed-angle bone screw shown in FIG. 6.

FIG. 12 is a partial cross-sectional view of the spinal stabilization system shown in FIG. 1, as engaged to a vertebra using the variable-angle bone screw shown in FIG. 7.

FIG. 14 is a top plan view of another embodiment of an elongate plate for use in association with the spinal stabilization system of FIG. 1.

FIG. 15 is a top plan view of another embodiment of an elongate plate for use in association with the spinal stabilization system of FIG. 1.

FIG. 16 is a top plan view of another embodiment of an elongate plate for use in association with the spinal stabilization system of FIG. 1.

FIG. 17 is a top plan view of another embodiment of an elongate plate for use in association with the spinal stabilization system of FIG. 1.

DESCRIPTION OF THE ILLUSTRATED EMBODIMENTS

Figure 6:
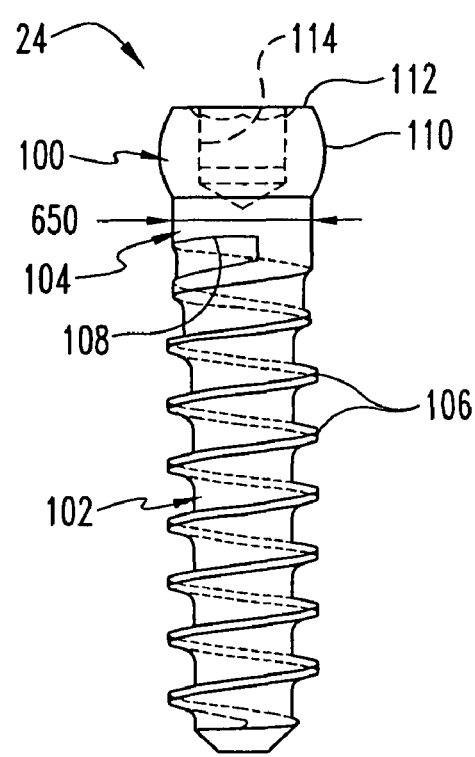
FIG. 6 is a side elevational view of one embodiment of a fixed-angle bone screw for use in association with the spinal stabilization system shown in FIG. 1.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Referring to FIGS. 1 and 2, shown therein is a spinal stabilization system 20 according to one form of the invention for use in stabilizing at least a portion of the spinal column. In one embodiment, stabilization system 20 is generally comprised of an elongate plate 22 positionable along a portion of the spinal column, a number of bone anchors 24 adapted to anchor plate 22 to the spinal column, and a number of retaining devices 26 adapted to engage the bone anchors 24 to prevent the bone anchors 24 from loosening and backing out of plate 22.

In one embodiment, stabilization system 20 is configured for attachment to the cervical region of the spinal column, spanning across a number of cervical vertebrae. However, it should be understood that stabilization system 20 may also be utilized in other areas of the spinal column, such as the thoracic, lumbar, lumbo sacral and sacral regions of the spine. It should also be understood that stabilization system 20 can extend across any number of vertebrae, including a pair of adjacent vertebrae or three or more vertebrae. Additionally, although stabilization system 20 is illustrated and described as having application in an anterior surgical approach, stabilization system 20 may alternatively be applied in other surgical approaches, such as, for example, antero-lateral, oblique and posterior surgical approaches.

In the illustrated embodiment, plate 22 extends along a longitudinal axis 21 and is sized to span a distance between at least two vertebral levels. However, it should be understood that plate 22 can take on other configurations, such as, for example, any type of elongate element suitable for use in stabilizing a portion of the spine. It should also be understood that any number of plates 22, including a pair of plates 22, may be used to provide stabilization to the spinal column. In one embodiment of the invention, plate 22 is formed of a metallic material such as, for example, stainless steel or titanium. However, it should be understood that plate 22 may be formed from a number of materials including, for example, a pure metallic composition, a metallic alloy, a shape-memory alloy, a polymer material, a synthetic material, a biologic material, and/or a resorbable material. Plate 22 is secured to cervical vertebrae 600 (FIGS. 11-13) by a plurality of the bone anchors 24. In one embodiment, bone anchors 24 are configured as bone screws. However, other types of bone anchors are also contemplated, such as, for example, bolts, hooks or other types of devices suitable for attaching plate 22 to vertebrae 600. Retaining devices 26 engage adjacent pairs of bone screws 24 to prevent the bone screws 24 from loosening and backing out. Retaining devices 26 may also be used to further secure plate 22 to the cervical vertebrae 600. In the illustrated embodiment, retaining device 26 includes a fastener that engages plate 22 and abuts against the heads of adjacent bone screws 24. However, other types of retaining devices are also contemplated, such as, for example, a pop rivet, a retainer, a lock washer rotatably displaceable between an unlocked position and a locked position, an expansion screw positioned in the head of the bone anchor to expand the head of the bone anchor, a retaining element integrally formed with the plate, or any other type of retaining element, device, mechanism or system. The retaining devices can be positioned on the plate to retain a single bone anchor or multiple bone anchors.

Referring to FIGS. 3-5, shown therein are further details regarding plate 22. Plate 22 includes multiple nodes or connection portions 32 that are configured to engage bone anchors 24 to attach plate 22 across multiple vertebral levels. The connection portions 32 are separated from one another by intermediate portions 34. Plate 22 has opposite end surfaces 36, 38, opposite side surfaces 40, 42, and opposite upper and lower surfaces 44, 46. The corners of plate 22 between end surfaces 36, 38 and side surfaces 40, 42 are rounded to eliminate sharp or abrupt edges that could pinch, cut or wear against tissue. The corners of plate 22 between upper surface 44 and the end and side surfaces 36, 38, 40 and 42 are also rounded to eliminate sharp or abrupt edges that could pinch, cut or wear against tissue.

When plate 22 is attached to the spinal column (FIGS. 11 and 12), the lower surface 46 abuts an outer vertebral surface. In one embodiment, lower surface 46 of plate 22 defines a concave lateral curvature 610 (FIG. 5) which corresponds to the anatomical lateral curvature of the vertebra 600. Lower surface 46 may also define a concave curvature 612 (FIG. 4) extending along longitudinal axis 21 which corresponds to the normal lordotic curvature of vertebra 600. In one embodiment, upper surface 44 of plate 22 defines a convex curvature that substantially corresponds to the concave curvatures 610, 612 of lower surface 46 to reduce the amount of trauma to the adjacent soft tissue when plate 22 is secured to the vertebrae 600 and to reduce the overall profile of plate 22. It should be understood, however, that plate 22 can take on other configurations to accommodate the specific spinal anatomy and pathology involved in the particular application of stabilization system 20.

In one embodiment, side surfaces 40, 42 of plate 22 adjacent the connection portions 32 have a convex configuration, while side surfaces 40, 42 adjacent intermediate portions 34 have a concave configuration. As a result, side surfaces 40, 42 have a serpentine shape or corrugated configuration defining a series of alternating ridges or peaks 50 and grooves or valleys 52. In the illustrated embodiment, each of the peaks 50 and valleys 52 has an arcuate shape so as to form an undulating curve or sinusoidal pattern extending along longitudinal axis 21. The rounded configuration of peaks 50 and valleys 52 minimizes stress concentrations and eliminates sharp or abrupt edges that could pinch, cut or wear against tissue. It should be understood, however, that peaks 50 and valleys 52 can take one other shapes and configurations, such as, for example, a triangular or rectangular shape so as to define a zigzag or tooth-like configuration.

In one embodiment of the invention, the upper and lower end surfaces 36, 38 of plate 22 define oppositely facings recessed areas 54 and 56, respectively. The recessed areas 54, 56 may be used to position and orient various types of instruments, templates, guides or other devices relative to plate 22. For example, recessed areas 54, 56 may be configured to receive a corresponding portion of a plate holder, drill guide and/or a screw guide to ensure proper positioning and orientation of the guide relative to plate 22. It should be understood that recessed areas 54, 56 need not necessarily be defined in end surfaces 36, 38, but may be defined in other portions of the elongate plate 22, such as, for example, the side surfaces 40, 42 or upper surface 44.

Figure 13:
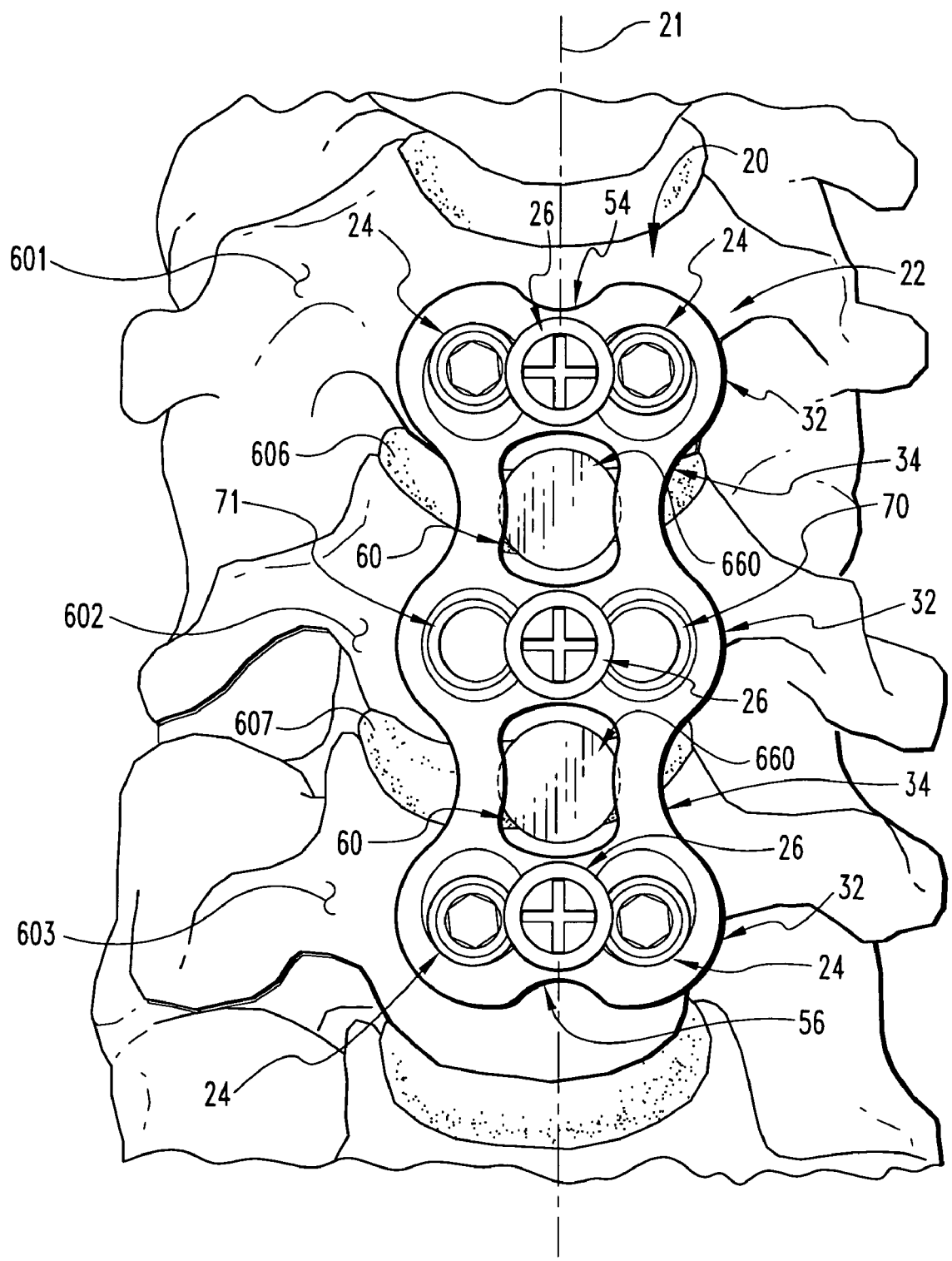
FIG. 13 is a top plan view of the spinal stabilization system shown in FIG. 1, as engaged to a plurality of vertebrae.

In one embodiment, connection portions 32 are spaced from one another by a distance 620 that substantially corresponds to the spacing between the adjacent cervical vertebrae to which plate 22 is attached (FIG. 13). Although connection portions 32 are illustrated as being offset from one another by a uniform distance 620, it should be understood that in other embodiments connection portions 32 may be offset from one another by non-uniform distances. As should be appreciated, intermediate portions 34 are spaced so as to be positioned adjacent a respective intervertebral disc space when plate 22 is attached to the cervical vertebrae (FIG. 13).

In one embodiment, plate 22 defines a first width 630 adjacent the connection portions 32 and a reduced second width 632 adjacent the intermediate portions 34. The reduced width 632 adjacent intermediate portions 34 decreases the outer contour and size of plate 22 to minimize the lateral extent of plate 22 in the area adjacent the intervertebral disc space. Additionally, the reduced width 632 adjacent intermediate portions 34 provides an area of reduced material to facilitate bending of plate 22 as may be required to conform plate 22 to the particular spinal anatomy to which plate 22 is attached.

In one embodiment, plate 22 includes a number of visualization openings or windows 60 extending through intermediate portions 34 between upper and lower surfaces 44, 46. Visualization openings 60 extend generally along longitudinal axis 21 of plate 22 and are generally positioned in the area adjacent the intervertebral disc space when plate 22 is attached to the cervical vertebrae (FIG. 13). Intermediate portion 34 includes a first member 61 extending along one side of visualization opening 60 and a second member 63 extending along the opposite side of visualization opening 60. In one embodiment, visualization openings 60 have an elongate hourglass-like configuration extending along virtually the entire length of the intermediate portions 34 and across a substantial portion of the width of the intermediate portions 34. However, it should be understood that other embodiments contemplate other sizes and shapes for the visualization openings 60.

In the illustrated embodiment, visualization openings 60 include a pair of opposite side walls 62, 64 extending between a pair of opposite end walls 66, 68. In one embodiment, side walls 62, 64 have a convex arcuate configuration that substantially corresponds to the outer contour of side surfaces 40, 42 defined along the intermediate portions 34 of plate 22. In this manner, the material width 634 of members 61, 63 between the outer side surfaces 40, 42 of the intermediate portions 34 and the side walls 62, 64 of the visualization openings 60 is substantially uniform. As a result, the elongate plate 22 is configured to provide optimum visualization capabilities via the inclusion of relatively large visualization openings 60 in combination with a reduced lateral profile in the areas adjacent the intermediate portions 34. The substantially uniform material width 634 provides plate 22 with sufficient load bearing strength while minimizing stress concentrations.

Visualization openings 60 define a minimum width 636 transversely to longitudinal axis 21. In one embodiment, width 636 is unobstructed and at least as great as the combined widths 634 of first and second members 61, 63 to provide optimal visualization capabilities through visualization opening 60 and around the sides of plate 22. Accordingly, visualization capabilities through plate 22 and on either side of plate 22 are enhanced. For example, unobstructed width 636 can range from 100 percent to about 150 percent of the combined widths 634 of first and second members 61, 63. In another example, unobstructed width 636 can range from 100 percent to about 125 percent of the combined widths 634 of first and second members 61, 63. Other embodiments contemplate an unobstructed width 636 that is less than the combined widths 634 of first and second members 61, 63. For example, unobstructed width 636 can range from 50 percent to less than 100 percent of the combined widths 634 of first and second members 61, 63. In another example, unobstructed widths 636 can range from 75 percent to less than 100 percent of the combined widths 634 of first and second members 61, 63.

In the illustrated embodiment, end walls 66, 68 of the visualization openings 60 have a concave arcuate configuration to maximize the size of the visualization openings 60 while maintaining sufficient load bearing strength of the plate 22. In one embodiment, visualization openings 60 have a maximum length along longitudinal axis 21 that allows viewing of the bony structure of the adjacent vertebrae therethrough. The corners formed between side walls 62, 64 and end walls 66, 68 are rounded to minimize stress concentrations and to eliminate sharp or abrupt edges that could pinch, cut or wear against tissue. Although visualization openings 60 have been illustrated with a particular shape and configuration, it should be understood that other embodiments contemplate other shapes and configurations of visualization openings 60, such as, for example, a rectangular, elliptical or circular configurations, convexly curved side walls and convexly curved end walls, concavely curved side walls and concavely curved end walls, convexly curved end walls and concavely curved side walls, and combinations thereof.

In one embodiment, each of the connection portions 32 includes a pair of bilateral openings 70, 71 configured to receive a respective pair of bone anchors 24 therein. The bone anchor openings 70, 71 extend entirely through plate 22 between the upper and lower surfaces 44, 46 and are disposed on opposite sides of longitudinal axis 21. Bone anchor openings 70, 71 are arranged along an axis 72, 73, respectively. In the illustrated embodiment, axes 72, 73 are inwardly tapered toward one another at an angle 640 (FIG. 5) relative to a transverse axis 23 defined through plate 22. Additionally, bone anchor openings 70, 71 extending through the outermost connection portions 32 (e.g. adjacent the end surfaces 36, 38) are outwardly tapered at an angle 642 (FIG. 4). In one embodiment, angle 640 is approximately 6 degrees and angle 642 is approximately 12 degrees. However, other angles 640, 642 are also contemplated.

Although the illustrated embodiment of plate 22 depicts each of the connection portions 32 as including a pair of bilateral bone anchor openings 70, 71, it should be understood that other configurations and arrangements are also contemplated. For example, each of the connection portions 32 may alternatively define a single bone anchor opening or three or more bone anchor openings. It should also be understood that the bone anchor openings 70, 71 need not necessarily extend though each of the connection portions 32, but may alternatively extend through select ones of the connection portions 32. It should also be understood that the bone anchor openings 70, 71 need not necessarily be arranged in a bilateral configuration, but may alternatively be arranged in other configurations, such as, for example, an axially offset configuration.

Aside from angular orientation, bone anchor openings 70, 71 are virtually identical, each being sized and configured to accept a corresponding one of the bone anchors 24 therein, the details of which will be discussed below. Each of the bone anchor openings 70, 71 includes a cylindrical-shaped portion 80 extending from the lower surface 46, a spherical-shaped recess portion 82 extending from the cylindrical-shaped portion 80, and a conical portion 84 extending from spherical-shaped recess portion 82 and opening onto upper surface 44. In one embodiment, the conical portion 84 is outwardly flared at approximately 45 degrees relative to the respective axes 72, 73. Although specific sizes and configurations of bone anchor openings 70, 71 have been illustrated and described herein, it should be understood that other sizes and configurations are also contemplated.

Each of the connection portions 32 also includes an aperture 90 configured to receive a respective one of the retaining devices 26 therein, the details of which will be discussed below. The apertures 90 extend through plate 22 between upper and lower surfaces 44, 46 and are positioned generally along longitudinal axis 21 between a laterally adjacent pair of bone anchor openings 70, 71. Each of the apertures 90 includes a threaded portion 92 extending from the lower surface 46 of plate 22 and a cylindrical-shaped countersunk portion 94 extending from the threaded portion 92 and opening onto upper surface 44. In one embodiment, the countersunk portion 94 intersects and overlaps at least a portion of each of the bone anchor openings 70, 71, and more particularly the spherical-shaped recess portion 82 of the bone anchor openings 70, 71. Although a specific size and configuration of the retaining device apertures 90 has been illustrated and described herein, it should be understood that other sizes and configurations are also contemplated. For example, apertures 90 need not necessarily extend entirely through plate 22, but may alternatively extend partially through plate 22 without penetrating lower surface 46. Apertures 90 may also be elongated to accept a retaining device longitudinally slidable or movable along or relative to plate 22.

Referring to FIG. 6, shown therein is one embodiment of a bone screw 24 suitable for use in association with spinal stabilization system 20. Bone screw 24 is of the fixed-angle type, the significance of which will become apparent below. Bone screw 24 includes a head portion 100 connected to a threaded shank portion 102 by an intermediate portion 104. Threaded shank portion 102 defines a number of threads 106 configured to engage vertebral bone and is sized to pass through the cylindrical-shaped portion 80 of bone anchor openings 70, 71 defined through plate 22. Threads 106 are adapted to engage cortical and/or cancellous bone. In one embodiment, bone screw 24 is configured as a self-tapping screw. In another embodiment, bone screw 24 is configured as a self-drilling screw. Threads 106 gradually transition into intermediate portion 104 by way of a thread run out 108.

Intermediate portion 104 of bone screw 24 has an outer diameter 650 that is slightly smaller than the inner diameter of the cylindrical-shaped portion 80 of bone anchor openings 70, 71. Head portion 100 includes a spherical-shaped surface 110 that is substantially complementary to the spherical-shaped recess portion 82 defined by bone anchor openings 70, 71. Head portion 100 additionally includes a truncated or flattened upper surface 112 through which extends a tool receiving recess 114 configured to receive a driving tool therein (not shown). In one embodiment, tool receiving recess 114 is a hexagonal recess. However, other shapes and configuration of tool receiving recesses are also contemplated.

Figure 7:
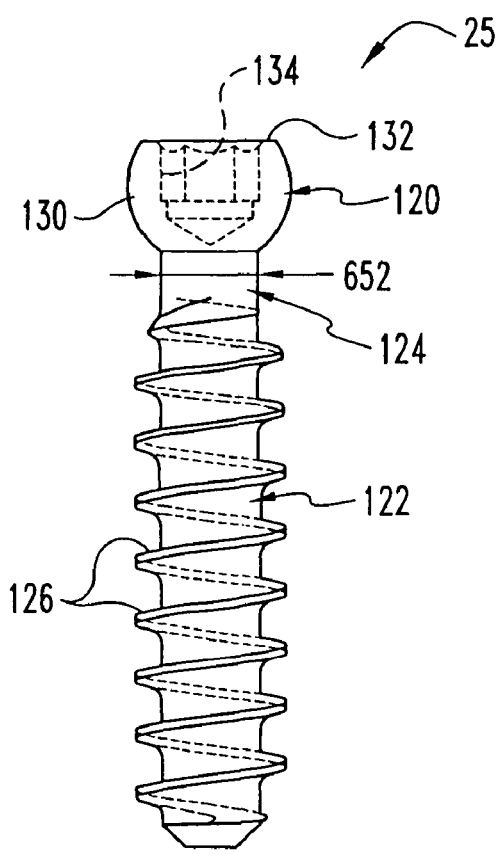
FIG. 7 is a side elevational view of one embodiment of a variable-angle bone screw for use in association with the spinal stabilization system shown in FIG. 1.

Referring to FIG. 7, shown therein is another embodiment of a bone screw 25 suitable for use in association with spinal stabilization system 20. Bone screw 25 is of the variable-angle type, the significance of which will become apparent below. Variable-angle bone screw 25 is configured similar to fixed-angle bone screw 24, including a head portion 120 connected to a threaded shank portion 122 by an intermediate portion 124. Threaded shank portion 122 defines a number of threads 126 configured to engage vertebral bone. Like fixed-angle bone screw 24, variable-angle bone screw 25 may also be configured as a self-tapping and/or a self-drilling screw. However, unlike intermediate portion 104 of bone screw 24, intermediate portion 124 of bone screw 25 has an outer diameter 652 that is significantly smaller than the inner diameter of the cylindrical-shaped portion 80 of bone anchor openings 70, 71, the significance of which will be discussed below. Head portion 120 includes a spherical-shaped surface 130 that is substantially complementary to the spherical-shaped recess portion 82 defined by the bone anchor openings 70, 71. Head portion 120 also includes a truncated or flattened upper surface 132 through which extends a tool receiving recess 134 configured to receive a driving tool therein (not shown).

Figure 8:
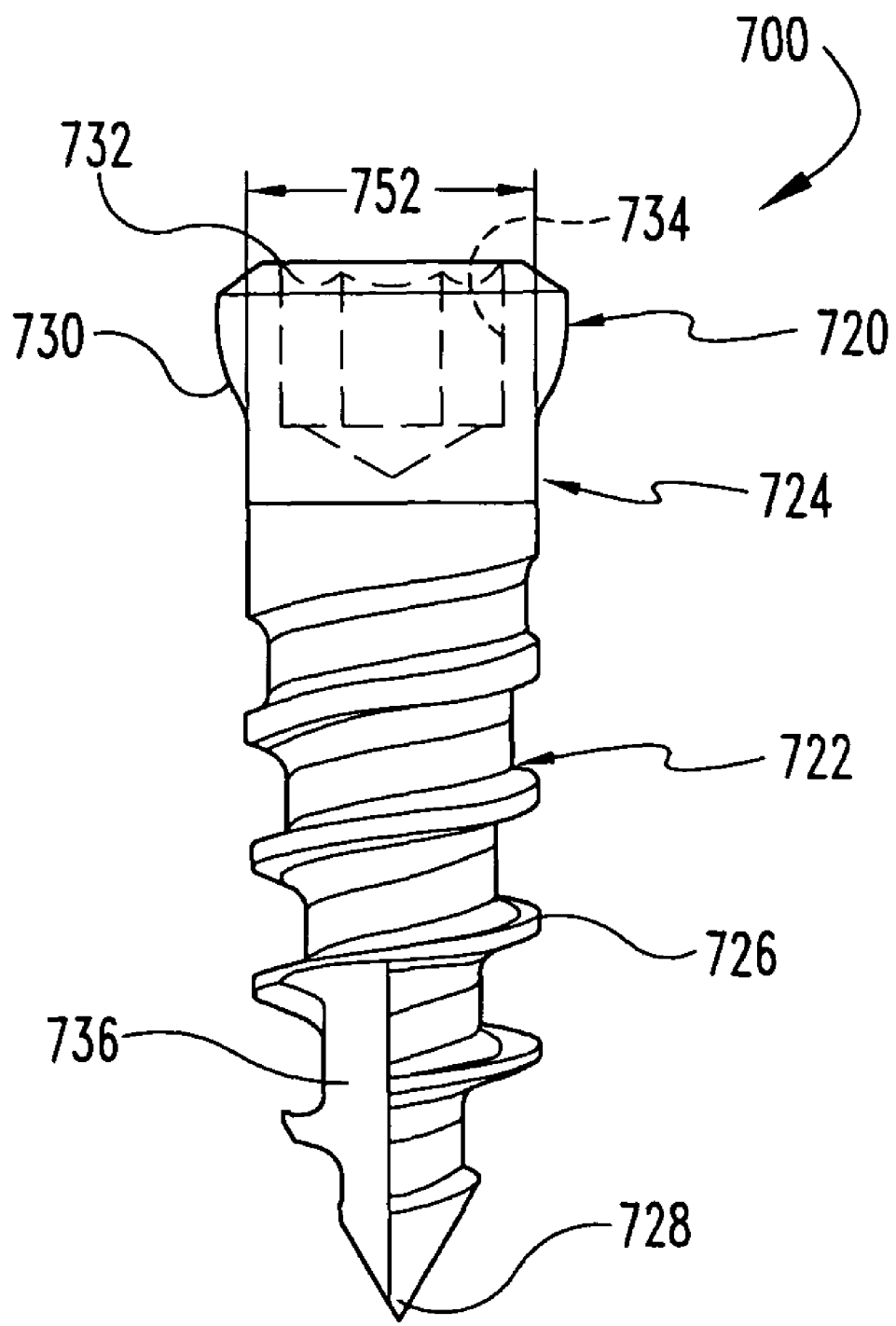
FIG. 8 is a side elevational view of one embodiment of a self-drilling bone screw for use in association with the spinal stabilization system shown in FIG. 1.

Referring to FIG. 8, shown therein is another embodiment of a bone screw 700 suitable for use in association with spinal stabilization system 20. Bone screw 700 is of the self-drilling fixed angle type. Bone screw 700 can also be provided with variable angle capabilities as discussed above with respect to bone screw 25. Self-drilling bone screw 700 includes a head portion 720 connected to a threaded shank portion 722 by an intermediate portion 724. Threaded shank portion 722 defines a number of threads 726 configured to engage vertebral bone. Intermediate portion 724 of bone screw 700 includes an outer diameter 752 that is sized to fit snugly in the bone anchor openings 70, 71 to provide a fixed angle relative to the plate when seated in openings 70, 71. Intermediate portion 724 could also be provided with a significantly smaller diameter to provide variable angle placement capabilities. Head portion 720 includes a spherical-shaped surface 730 that is substantially complementary to the spherical-shaped recess portion 82 defined by the bone anchor openings 70, 71. Head portion 720 also includes a truncated or flattened upper surface 732 through which extends a tool receiving recess 734 configured to receive a driving tool therein (not shown). The distal tip of shank 722 includes a sharp point 728 to facilitate penetration into bone, and a relieved portion 736 to facilitate passage into the undrilled, untapped bony structure.

Referring to FIGS. 9 and 10, shown therein are various details regarding retaining device 26. In one embodiment, retaining device 26 is generally comprised of a fastener 150 and a washer 152. Although a specific configuration of retaining device 26 has been illustrated and described herein, it should be understood that other configurations of retaining devices are also contemplated as discussed above.

Fastener 150 includes a head portion 154 and a threaded shank portion 156 extending therefrom. Threaded shank portion 156 defines a number of machine threads 158 configured to engage threaded portion 92 of aperture 90 defined by plate 22. Threaded shank portion 156 terminates in a sharp point 160 to aid in the insertion of fastener 150 into threaded portion 92 of aperture 90 and to facilitate penetration into vertebral bone. Head portion 154 includes an outwardly tapering conical surface 162. In one embodiment, conical surface 162 defines a taper angle of approximately 45 degrees. Head portion 154 further includes an upper surface 164 through which extends a tool receiving recess 166 configured to receive a driving tool (not shown). In one embodiment, tool recess 166 is a Phillips-type recess. However, other types and configurations of tool receiving recesses are also contemplated.

Washer 152 has an outer surface including a lower tapered portion 170 and an upper non-tapered portion 172. Washer 150 also defines an opening 174 extending therethrough having a lower non-tapered portion 176 and an upper tapered portion 178. Upper tapered portion 178 is substantially complementary to outer conical surface 162 of fastener 150. Engagement between outer conical surface 162 of fastener 150 and tapered portion 178 of washer opening 174 facilitates self-centering of fastener 150 within washer 152. Non-tapered portion 176 of washer opening 172 is sized to receive threaded portion 156 of fastener 150 therethrough for engagement with threaded portion 92 of aperture 90 defined by plate 22.

Referring to FIG. 11, shown therein is plate 22 attached to a vertebra 600 via the fixed-angle bone screws 24. Initially, plate 22 is positioned along the spinal column so as to extend between at least two vertebrae, with lower surface 46 positioned in abutment against an outer surface of vertebra 600. Connection portions 32 of plate 22 are then secured to the vertebra 600 by passing threaded portions 102 of bone screws 24 through respective ones of the bone anchor openings 70, 71 and driving threaded portions 102 into vertebral bone by way of a driver (not shown) engaged within the tool receiving recess 114 (FIG. 6). Conical portion 84 of bone anchor openings 70, 71 serves to facilitate insertion of bone screws 24 into bone anchor openings 70, 71 and/or to aid in positioning and orientation of screw guides, drill guides, drills or other instrumentation (not shown) relative to plate 22.

Once plate 22 is properly positioned and oriented relative to vertebra 600, bone screws 24 are driven into vertebral bone until the lower portion of the spherical surface 110 of screw head 100 is positioned in abutment against the spherical-shaped recess portion 82 of bone anchor opening 70, 71, with the intermediate portion 104 of the bone screw 24 positioned within the cylindrical-shaped portion 80 of bone anchor openings 70, 71. The relatively close tolerance between intermediate portion 104 of bone screw 24 and cylindrical-shaped portion 80 of bone anchor openings 70, 71 orients bone screws 24 at a fixed angle along bone anchor axes 72, 73 and substantially prevents pivotal or translational movement of bone screws 24 relative to plate 22. The spherical-shaped recess portions 82 also act as a countersink for head portions 100 of bone screws 24, thereby allowing a significant portion of screw heads 100 to be positioned beneath upper surface 44 of plate 22 to minimize the overall height or profile of spinal stabilization system 20.

Once bone screws 24 are fully driven into vertebra 600 and plate 22 is securely attached to vertebra 600, retaining devices 26 are installed to prevent bone screws 24 from loosening and backing out of plate 22. Threaded shank portion 156 of fastener 150 is initially inserted through non-tapered portion 176 of opening 174 in washer 152. Threaded shank portion 156 is then threaded into threaded portion 92 of aperture 90 by way of a driver (not shown) engaged within tool receiving recess 166. As fastener 150 is driven through threaded portion 92 of aperture 90, pointed end 160 penetrates into vertebral bone, thereby further securing elongate plate 22 to the vertebra 600. Additionally, by embedding threaded portion 92 within vertebral bone, fastener 150 is less likely to loosen and back out of plate 22. Fastener 150 continues to be threaded through the aperture 90 until lower conical surface 162 of fastener head 154 engages tapered portion 178 of washer opening 174, which in turn engages outer conical surface 170 of washer 152 tightly against the upper portion of spherical surface 110 of bone screw head 100. Engagement of washer 152 against bone screw head 110 prevents bone screws 24 from loosening and backing out of plate 22.

Referring to FIG. 12, shown therein is plate 22 attached to vertebra 600 via variable-angle bone screws 25. Variable-angle bone screws 25 co-act with plate 22 and retaining device 26 in a manner similar to that described above with regard to the fixed-angle bone screws 24. However, with regard to variable-angle bone screws 25, since intermediate bone screw portion 124 is sized significantly smaller than cylindrical-shaped portion 80 of bone anchor openings 70, 71, a gap 654 exists between the intermediate bone screw portion 124 and plate 22. This gap 654 permits bone screws 25 to pivot or toggle within the bone anchor openings 70, 71 relative to the bone anchor axes 72, 73, thereby allowing bone screws 25 to be positioned at a variable angle relative to plate 22. It is understood that the degree of angulation of bone screws 25 is limited by the size of gap 654 between the intermediate bone screw portion 124 and plate 22. In one embodiment, gap 654 is sized to permit angulation of bone screws 25 up to 20 degrees in any direction relative to bone anchor axes 72, 73. Other angulations for bone screws 25 are also contemplated, ranging from 0 degrees to 45 degrees, for example.

The variable-angle capability provided by bone screw 25 allows the surgeon to engage bone screw 25 to the vertebra 600 at any angle within the defined angulation limits, thereby providing greater flexibility in orienting bone screws 25 at a select angle to accommodate the particular anatomy of the vertebra 600 and/or the pathology being treated. Moreover, this variable-angle capability provided by bone screws 25 permits a limited degree of micro-motion or translation between bone screws 25 and plate 22, which may prevent or at least reduce the build-up of load stresses within stabilization system 20. It should be understood that in certain embodiments, a combination of fixed-angle bone screws 24 and variable-angle bone screws 25 may be used to secure plate 22 to vertebra 600.

Referring to FIG. 13, shown therein is plate 22 attached to the cervical region of the spinal column. More particularly, plate 22 is sized to span multiple vertebral levels, with the connection portions 32 attached to a number of cervical vertebrae 601, 602, 603 via bone anchors 24, 25 and/or the fasteners 150 of the retaining devices 26. When plate 22 is secured to vertebrae 601, 602, 603, intermediate portions 34 and visualization openings 60 are positioned approximately adjacent respective intervertebral disc spaces 606, 607. Additionally, the reduced width 632 of intermediate portions 34 relative to the connection portions 32 provides plate 22 with a reduced lateral profile in the areas adjacent the intervertebral disc spaces 606, 607.

Visualization openings 60 and the reduced lateral profile of the intermediate portions 34 of plate 22 provide the capability to visualize the intervertebral disc spaces 606, 607 and/or spinal implants 660 or other devices or instruments positioned within the intervertebral disc spaces 606, 607. More specifically, these features provide for direct visualization of implants 660 disposed within the intervertebral disc spaces 606, 607, the relationship between plate 22 and implants 660, and/or the interface between implants 660 and the vertebral endplates. As mentioned above, such implants 660 may include, for example, a bone graft, an artificial fusion device, or any other type of interbody device that is insertable within the intervertebral disc space. Further examples of such implants include bone dowels, push-in type cages, screw-in type cages, tapered cages, cages filled with bone graft and/or graft substitute material or other types of devices suitable for fusion applications, external or internal stabilization of a segment of the spinal column or other types of bony segments.

It should be understood that stabilization system 20 can be used in conjunction with fusion-type implants that promote fusion between adjacent pairs of vertebrae and/or spacer-type implants that serve to maintain a spacing between adjacent pairs of vertebrae. In applications involving fusion type implants, plate 22 provides temporary stabilization during the fusion process. Following fusion of the adjacent vertebrae, plate 22 may be removed from the patient, may be maintained within the patient, or may be formed of a resorbable material that is resorbed into the patient over a period of time.

In the illustrated embodiment shown in FIG. 13, a single implant 660 is centrally disposed within each of the intervertebral disc space 606, 607. In this case, visualization openings 60 provide the primary means for direct visualization of implants 660 in relation to the intervertebral disc spaces 606, 607. However, in other embodiments, a pair of implants 660 may be inserted bilaterally within each of the intervertebral disc space 606, 607. In this instance, the reduced lateral profile of the intermediate portions 34 of plate 22 provides an additional feature for direct visualization of implants 660 in relation to vertebrae 601, 602, 603 and intervertebral disc spaces 606, 607.

The direct visualization capabilities offered by plate 22 eliminates, or at least minimizes, the need to verify intraoperative or post-operative placement and positioning of implants 660 within intervertebral disc spaces 606, 607 (e.g., verification of the interface between the implant and the vertebral endplates, the lateral positioning of the implant within the disc space, the relationship between the implant and the elongate plate, etc.). As a result, the need for additional x-rays or other radiographic imaging techniques is significantly reduced, thereby minimizing the patient's exposure to radiation. Likewise, the time required to implant plate 22 and/or the implants 660 is also significantly reduced. Additionally, the surgeon is provided with added confidence regarding the proper placement of plate 22 and/or the implants 660 relative to vertebrae 601, 602, 603 and intervertebral disc spaces 606, 607.

Other embodiments provide visualization features in place of or in addition to those features illustrated and described above with regard to spinal stabilization system 20. For example, a plate may be provided that is at partially formed from a translucent material to provide direct visualization of one or more implants disposed within intervertebral disc spaces, the relationship between the plate and the implants, and/or the interface between the implants and the vertebral endplates. In one embodiment, the entire plate may be formed of a translucent material. In another embodiment, only the portions of the plate that are positioned approximately adjacent the intervertebral disc space are formed of a translucent material, with the remainder of the plate, including the portions that are connected to the vertebrae, formed of conventional materials such as stainless steel or titanium. It should be understood that a variety of materials may be used to provide visualization capabilities to the plate, including various types of translucent materials, partially-translucent materials, transparent materials, semi-transparent materials, or any other material that allow a sufficient amount of light to pass therethrough. Such materials include, for example, various types of plastic materials or polymeric materials.

In another embodiment, the plate may be designed to have a modular configuration to provide visualization of the implant and/or the vertebral anatomy during placement of the plate and/or the implant. For example, select portions of the plate may be removed to provide direct visualization capabilities at various stages of the implant/plate placement procedure. The removed portions may be subsequently replaced or obscured after the placement procedure is complete. For example, certain portions of the plate positioned adjacent the intervertebral disc space may be configured for selective removal to provide enhanced visualization of the implant and/or the vertebral anatomy at various stages of the implant/plate placement procedure. The removable portions may subsequently be reassembled with the remainder of the plate to strengthen the plate and/or to conceal, cover or otherwise obscure the visualization site.

Although the above-discussed embodiments provide direct visualization capabilities involving viewing with the naked eye, it should be understood that other means and/or methods may be used to provide indirect visualization capabilities in place of or in addition to the direct visualization capabilities discussed above. For example, a plate may be provided which is at partially formed from a radiolucent material to provide indirect visualization via the use of x-rays or other radiographic imaging techniques. In one embodiment, the entire plate may be formed of a radiolucent material. In another embodiment, only the portions of the plate that are positioned adjacent the intervertebral disc space are formed of a radiolucent material, with the remainder of the plate, including the portions that are connected to the vertebrae, formed of conventional materials such as stainless steel or titanium.

Various techniques, devices and instrumentation are provided to position the plate in relation to the vertebrae and to engage the plate to the vertebrae. These techniques, devices and instrumentation are designed and/or configured in such a manner as to minimize interference with the visualization capabilities provided by the plate and/or to provide independent visualization capabilities.

In one embodiment, self-drilling bone screws may be used to secure the plate to the vertebrae, thereby eliminating use of a drill guide which could potentially interfere with the visualization capabilities provided by the plate. In another embodiment, the instrumentation used to position and attach the plate to the vertebrae may be formed from materials that provide some degree of visualization. Such instrumentation may include, for example, templates, plate holders, bone screw guides, drivers, or other instruments or devices typically associated with the placement and attachment of a plate to a number of vertebrae. In one embodiment, various portions of the instrumentation may be formed of a translucent material or a radiolucent material to provide enhanced visualization capabilities to the spinal fixation system. In another embodiment, the design of the instrumentation may take into account various geometric considerations that provide enhanced visualization capabilities and minimization of interference with the visualization capabilities provided by the plate.

Referring to FIGS. 14 and 15, shown therein are plates 200 and 300, respectively, according to other embodiments of the stabilization system 20. Plates 200 and 300 are configured similar to plate 22 illustrated and described above. However, the connection portions 32 of plate 200 are spaced from one another by a distance 621 which is less than distance 620 separating connection portions 32 of plate 22. As a result, the visualization openings 60 defined by plate 200 have a lesser length-to-width aspect ratio than do visualization openings 60 defined by plate 22. With regard to plate 300, the connection portions 32 are spaced from one another by a distance 622, which is greater than distance 620 separating connection portions 32 of plate 22. As a result, visualization openings 60 defined by plate 300 have a greater length-to-width aspect ratio than do visualization openings 60 defined by plate 22.

As should be appreciated, the distance separating connection portions 32 of plates 22, 200 and 300 may be selected to match the particular spacing between the vertebrae to which the plates are attached. As should also be appreciated, the connection portions 32 may be spaced apart so as to position the intermediate portions 34 of the plate adjacent respective ones of the intervertebral disc spaces. It should also be appreciated that the distance separating adjacent pairs of the connection portions 32 need not necessarily be uniform. Instead, the distance separating adjacent pairs of connection portions 32 can be selected to accommodate the particular spinal anatomy to which the plate is attached.

Referring to FIGS. 16 and 17, shown therein are plates 400 and 500, respectively, according to other embodiments of the stabilization system. Plates 400 and 500 are configured similar to plate 22 illustrated and described above. However, unlike plate 22 which includes three connection portions 32 for attachment across three vertebral levels, plate 400 includes four connection portions 32 for attachment across four vertebral levels, while plate 500 includes a pair of connection portions 32 for attachment across two vertebral levels. As should be appreciated, the plates used in association with the present invention can be readily adapted to span any number of vertebral levels by appropriately sizing plate 22 and by providing plate 22 with the appropriate number of connection portions 32.

Various length-to-width aspect ratios for visualization openings are contemplated to provide optimal visualization capabilities. In some embodiments, such as shown in FIG. 14, length 638 is less than the width 636 of visualization opening 60 due to the overall length constraints for the plate imposed by anatomical considerations. Length-to-width aspect ratios ranging from 0.5 to 1.0 are contemplated for these embodiments. In other embodiments, the maximum length 638 to minimum width 636 aspect ratios of visualization openings 60 the plate are greater than 1.0. In some embodiments, length-to-width aspect ratios of 1.0 to about 2.5 are contemplated. Other embodiments contemplate length-to-width aspect ratios ranging from about 1.0 to about 1.5. Still other embodiments contemplate length-to-width aspect ratios ranging from about 1.5 to about 2.25. Further embodiments contemplate length-to-width aspect ratios ranging from about 1.0 to about 2.0.

Figure 18:
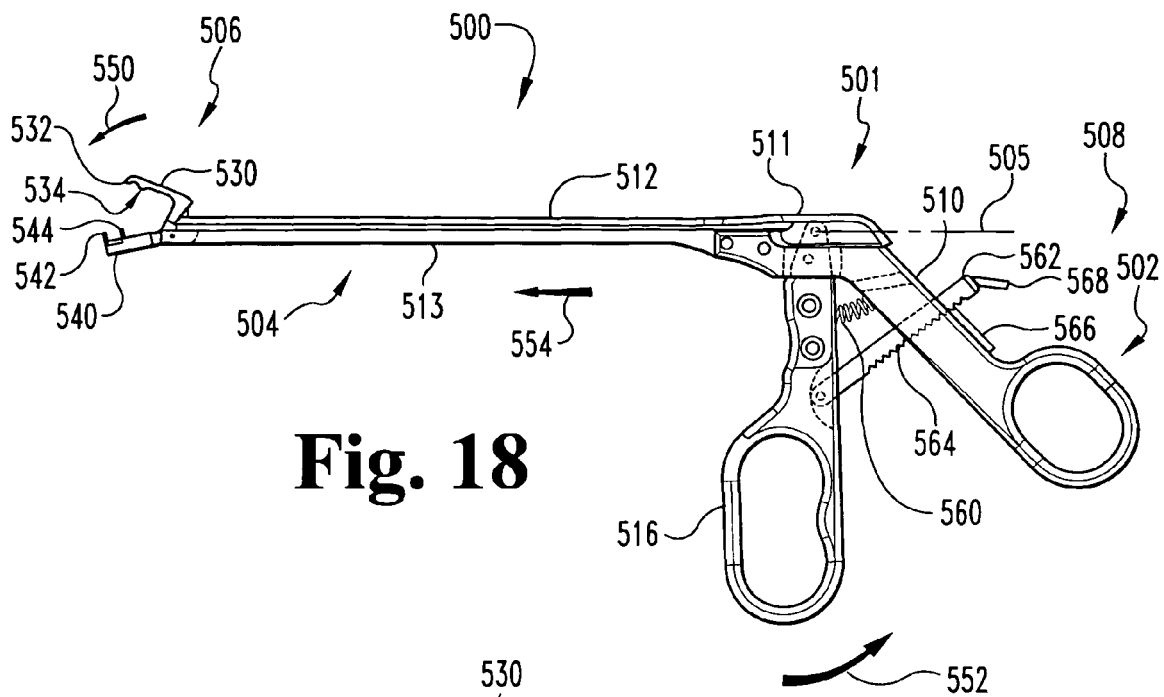
FIG. 18 is an elevational view of a holding instrument engageable to a plate to facilitate positioning of the plate at the operative site.

Referring to FIG. 18 there is shown a holding instrument 500 for holding a plate, such as any of the plate embodiments discussed herein, for positioning the plate adjacent to the spinal column. Holding instrument 500 assists the surgeon in maintaining the position of the plate as bone engaging fasteners or anchors are positioned through the plate holes. Holding instrument 500 includes a holding system 506 at a distal end of an actuating system 501. A locking system 508 is provided to maintain holding system 506 in engagement with the plate or other implant.

Figure 21:
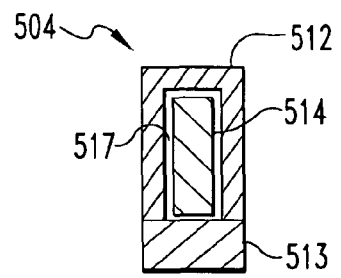
FIG. 21 is a section view through line 21-21 of FIG. 19.

Actuating system 501 includes a handle system 502 and a connecting system 504 operable to move holding system 506 between a position engaged or clamped with the plate and a position released from the plate. Handle system 502 includes a first handle portion 510 and a second handle portion 516 pivotally secured to a frame portion 511 of first handle portion 510. Connecting system 504 includes a first member 512 coupled at its proximal end to frame portion 511 of first handle portion 510, and a second member 513 coupled at its proximal end 546 (FIG. 22) to frame portion 511 of first handle portion 510. As further shown in FIGS. 19 and 21, first member 512 includes a channel 517 therethrough for receiving a linkage 514. Linkage 514 is pivotally coupled at its proximal end to second handle portion 516 and movable relative to first and second members 512, 513 in channel 517 in response to movement of second handle portion 516 relative to first handle portion 510. Movement of linkage 14 manipulates holding system 506 between a clamped or engaged position and a release position.

Figure 22:
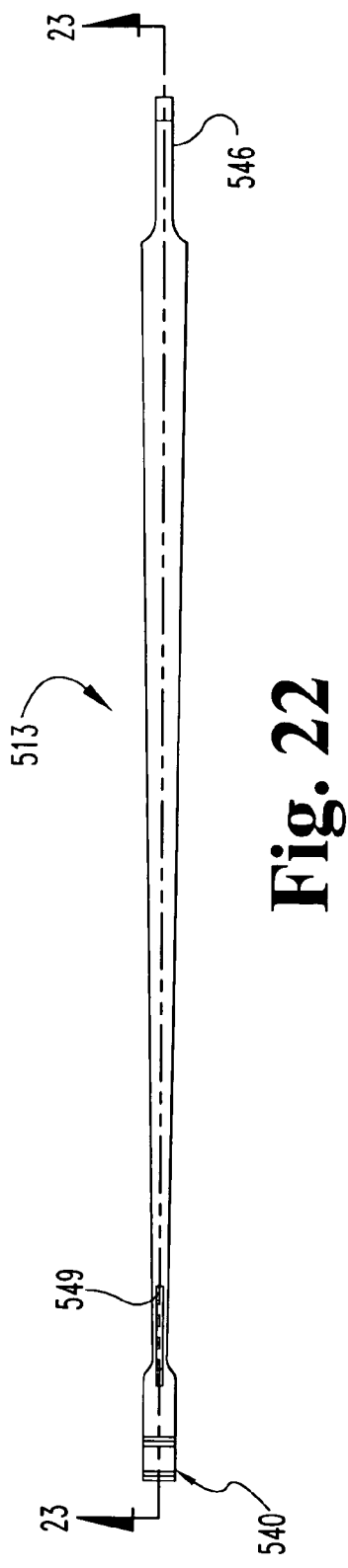
FIG. 22 is a plan view of a second member comprising a portion of the holding instrument of FIG. 18.
Figure 23:
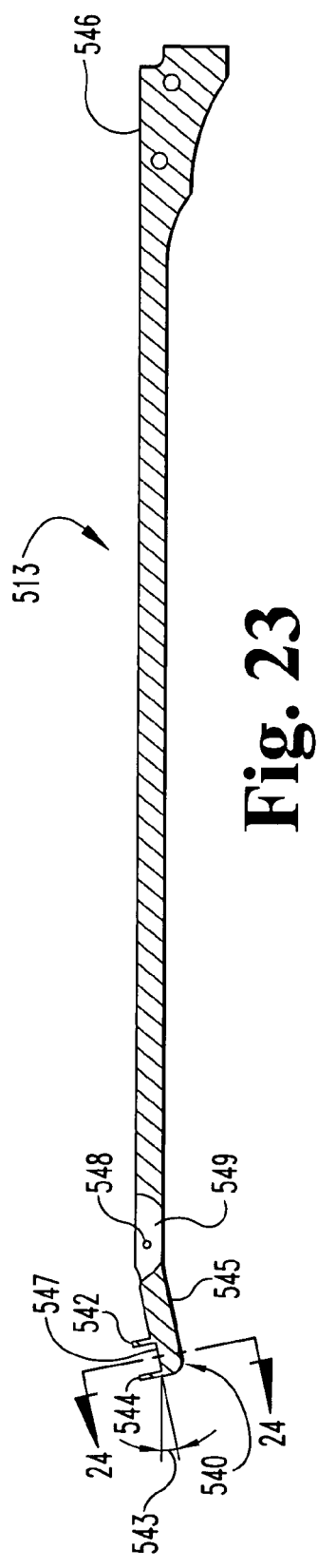
FIG. 23 is a section view through line 23-23 of FIG. 22.
Figure 24:
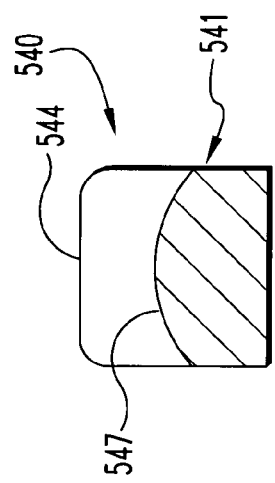
FIG. 24 is a section view through line 24-24 of FIG. 23.

Holding system 506 includes a first holding member 530 (FIGS. 19 and 20) and a second holding member 540 (FIGS. 22-24.) In the illustrated embodiment, second holding member 540 is at located at the distal end of second member 513 and integral therewith. A receptacle 549 is formed in second member 513 and proximally located relative to holding member 540. It is further contemplated that, as shown in FIG. 23, second holding member 540 can extend relative to a proximal portion of second member 513 at an angle 543 to facilitate engagement of the plate at a desired angular orientation relative to longitudinal axis 505 of holding instrument 500.

First holding member 530 includes a proximal portion 531 pivotally coupled to a distal end of linkage 514 via pin 533. Proximal portion 531 can be provided with a reduced width that allows proximal portion 531 to be received in receptacle 549. Proximal portion 531 further includes a bore 535 to receive a pin to pivotally couple proximal portion 531 with bore 548 in receptacle 549 of second member 513. First holding member 530 is thus pivotal relative to second member 513 via actuation of linkage 514 with handle portion 516 while second holding member 540 remains in a fixed position.

Figure 27:
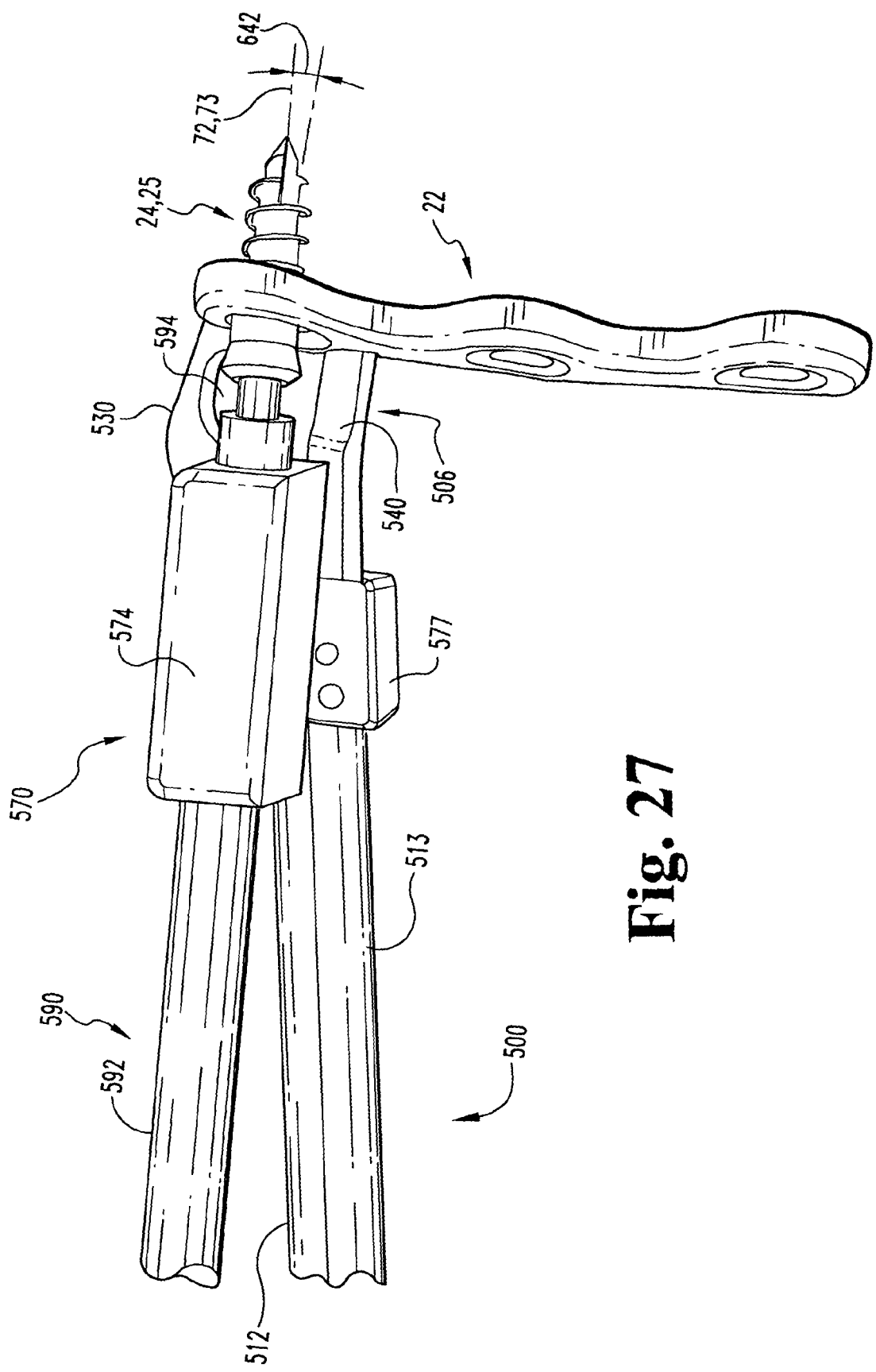
FIG. 27 is an elevational view of a distal portion of the holding instrument of FIG. 26 secured to a plate and a bone engaging fastener being guided through the plate with the guide mechanism.

Reciprocation of linkage 514 with handle system 502 moves linkage 514 in first member 512 and thus first holding member 530 between first and second positions relative to second holding member 540. In the first position, such as shown in FIG. 18, first holding member 530 is pivoted away from second holding member 540 for positioning of a portion of a plate or other implant therebetween. In the second position, such as shown in FIG. 27, first holding member 530 is moved toward second holding member 540 for gripping or clamping the plate or implant therebetween.

Figure 19:
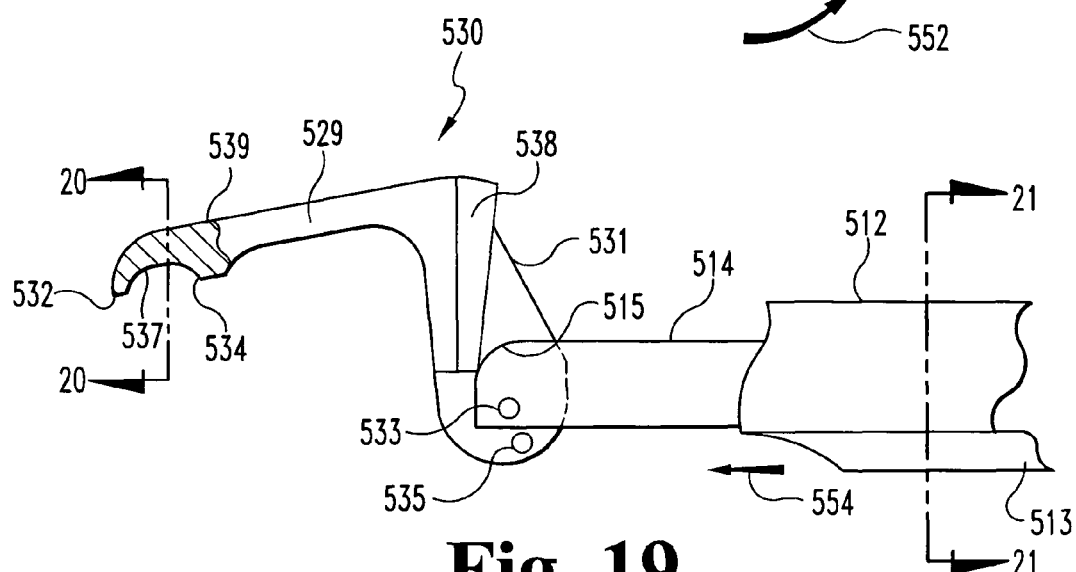
FIG. 19 is an elevational view of a distal portion of the holding instrument of FIG. 18.
Figure 20:
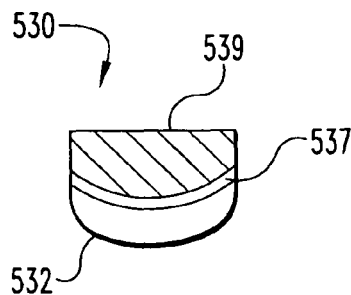
FIG. 20 is a sectional view through line 20-20 of FIG. 19.

Holding system 506 can be adapted to provide secure gripping or clamping of the implant between holding members 530, 540. For example, as shown in FIGS. 19-20, holding member 530 includes an engagement member 539 having a distal flange 532, a proximal flange 534, and a contacting surface 537 therebetween that includes a convex curvature transverse to longitudinal axis 505 of holding instrument 500. When clamped to an end wall or end surface of plate 22, for example, distal flange 532 can be positioned along bottom surface 46 of plate 22, while proximal flange 534 can be positioned along upper surface 44 of plate 22. The convexly curved contact surface 537 can match the concave surface profile of a plate surface against which it is to be positioned, such as end surface 36 of plate 22. Plate 22 can include receptacles or recesses to facilitate placement of holding members 530, 540 in the desired position relative to plate 22. For example, contact surface 537 can conform to the curvature of recess 54 of plate 22.

Similarly, second holding member 540 includes an engagement member 541 having a distal flange 544, a proximal flange 542, and a convexly curved contact surface 547. When clamped to an end wall or end surface of plate 22, for example, distal flange 544 can be positioned along bottom surface 46 the plate 22, and proximal flange 542 can be positioned along upper surface 44 of plate 22. Contacting surface 547 can contact an end wall of plate 22, such as upper wall 66 of upper visualization openings 60 or bottom end surface 38.

The convexly curved contact surfaces 537, 547 of holding members 530, 540 provide an evenly distributed clamping force along the end wall engaged, and provide firm gripping of the end walls of the plate therebetween. It is contemplated that holding members 530, 540 could also be positioned relative to the plate to clamp, for example, end walls 68, 66 of adjacent visualization openings 60, or the lower end wall 68 of a lower visualization opening and bottom end surface 38 of plate 22. By engaging plate 22 along adjacent end walls or end surfaces, visualization opening 60 remains substantially unobstructed by holding instrument 500. In addition, the lateral profile of connecting system 504 and holding system 506 can be minimized to minimize the lateral extent and obstruction of holding instrument 500 with bone engaging fastener holes 70, 71 and also to facilitate visualization along lateral side surfaces 40, 42.

Contacting surfaces 537, 547 can be provided with other surface profiles to conform to the surface of the plate to be engaged. For example, either or both of the contacting surfaces 537, 547 can be concavely curved to conform to a convexly curved plate surfaces. Contacting surface 537, 547 can be provided with teeth, ridges, barbs or other surface features to enhance gripping with the plate.

In one embodiment, it is contemplated that movement of first holding member 530 in the direction of arrow 550 is effected by moving second handle portion 516 in the direction of arrow 552, thereby moving linkage 514 distally in the direction of arrow 554 relative to first member 512 and second member 513. Distal movement of linkage 514 positions camming surface 515 of linkage 514 in contact with an abutment portion 538 of first holding member 530. Linkage 514 can thus, in addition to pushing on pin 533, push distally on abutment portion 538 of first holding member 530 to rotate it in the direction indicated by arrow 550. In one embodiment, proximal portion 531 extend transversely to longitudinal; axis 505 to offset engagement member 539 from engagement member 541 when holding members 530, 540 are moved to there clamped position. This provides space for positioning of the portion of the plate between the adjacent end walls therebetween.

Holding member 530 includes an intermediate portion 529 between proximal portion 531 and engagement member 539. Holding member 540 include intermediate portion 545 between engagement member 541 and receptacle 549. Intermediate portions 529, 545 extending generally in the direction of longitudinal axis 505, and provide a gap or space between holding members 530, 540 extending along longitudinal axis 505 to facilitate viewing of the plate portion clamped therebetween.

The clamping force applied to the plate clamped between holding members 530, 540 can be maintained with locking system 508. To release the plate, locking system 508 is released so that handle portion 516 can be moved in the direction opposite arrow 552 to separate first holding member 530 from second holding member 540. This movement of handle portion 516 pulls linkage 514 proximally to pivot first holding member 530 in the direction opposite arrow 550 relative to second member 513. A spring mechanism 560 can be provided between first handle portion 510 and second handle portion 516 to bias holding system 506 toward the released position and facilitate release of the plate or implant clamped or engaged therebetween.

In the illustrated embodiment, locking system 508 includes a locking arm 562 having a ratchet surface 564 located along one side thereof. Locking arm 562 is pivotally attached to second handle portion 516, and extends through a passage formed through first handle portion 510. Ratchet surface 564 is moveable into engagement with one or more locking members 566 on first handle portion 510. A grasping portion 568 facilitates the surgeon in rotating locking arm 562 away from locking member 566 when it is desired to release the plate or implant secured in holding system 506. It is contemplated that locking member 566 and ratchet surface 564 can be configured to allow incremental movement of handle portion 516 in the direction of arrow 552. Locking member 566 engages one or more of the teeth comprising ratchet surface 564, and then automatically locks second handle portion 516 in the moved position to prevent movement of second handle portion 516 in the direction opposite arrow 552 unless locking arm 562 is released.

In one embodiment, holding instrument 500 has application with spinal plates to provide a low profile at the surgical site, facilitating visualization of the surgical site and minimizing obstruction of the holding instrument with other instruments and implants at the surgical site. Other applications of holding instrument 500 include surgical procedures for implanting other implants where visualization is desired. Connecting system 504 can include tubular elements, rod-like elements, linkages, elastically-deformable members, and articulating connectors, for example. Handle system 502 can include handles to facilitate the surgeon's control of the depth, angular orientation and rotational orientation of holding system 506 and the implant held thereby. Other suitable examples of handle systems 502 include t-bars, pistol-grips, hooks, circular finger controls, co-axial shafts, and side-by-side shafts. Lock system 508 includes any device or mechanism capable of releasably securing holding system 506 to the implant. Suitable examples of locking system 508 include force-fit or wedge-type locking mechanisms, pivoting lock mechanisms, rotating lock mechanisms, geared lock mechanisms, etc.

Figure 25:
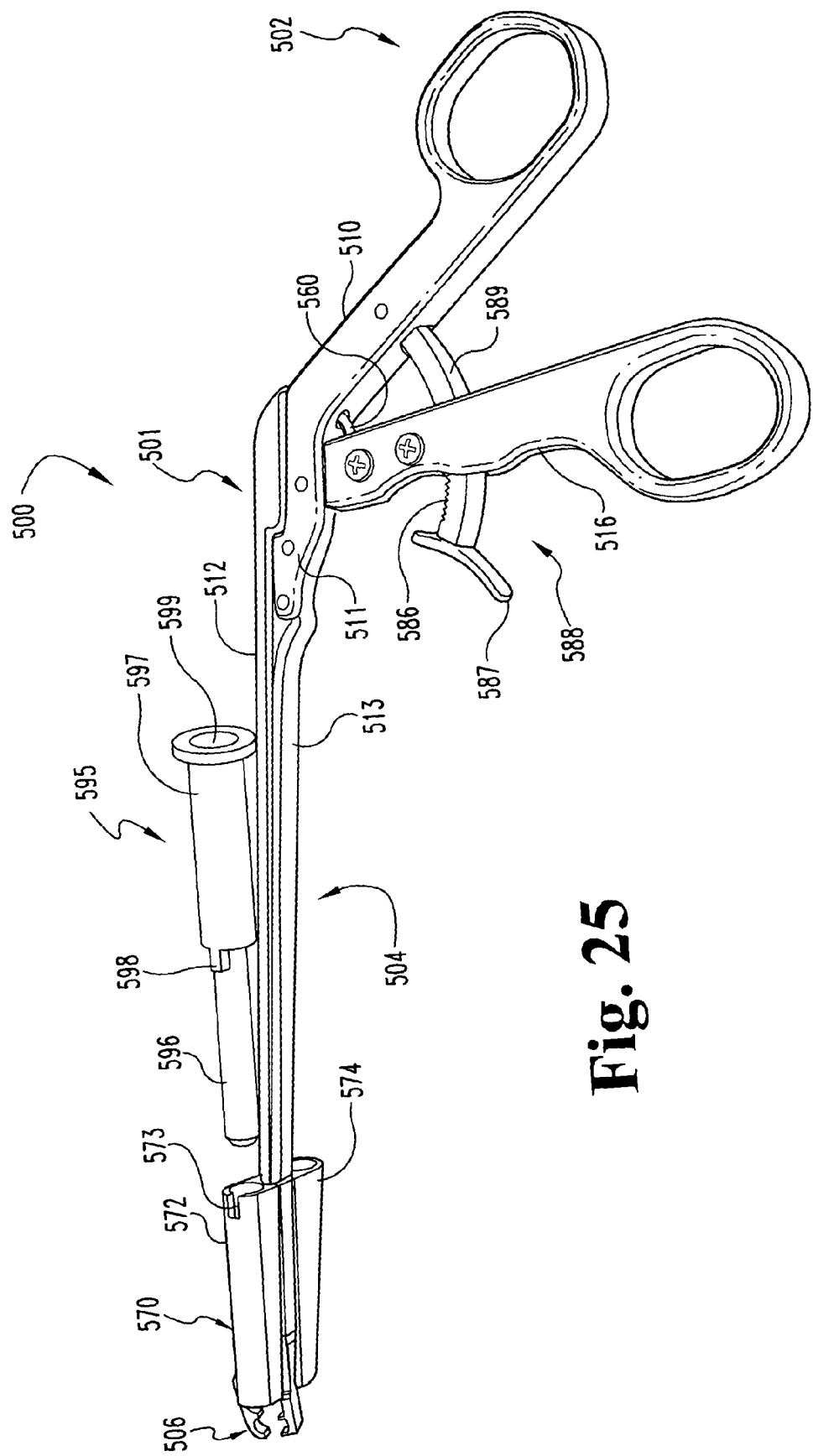
FIG. 25 is an elevational view of another embodiment holding instrument including a guide mechanism.
Figure 26:
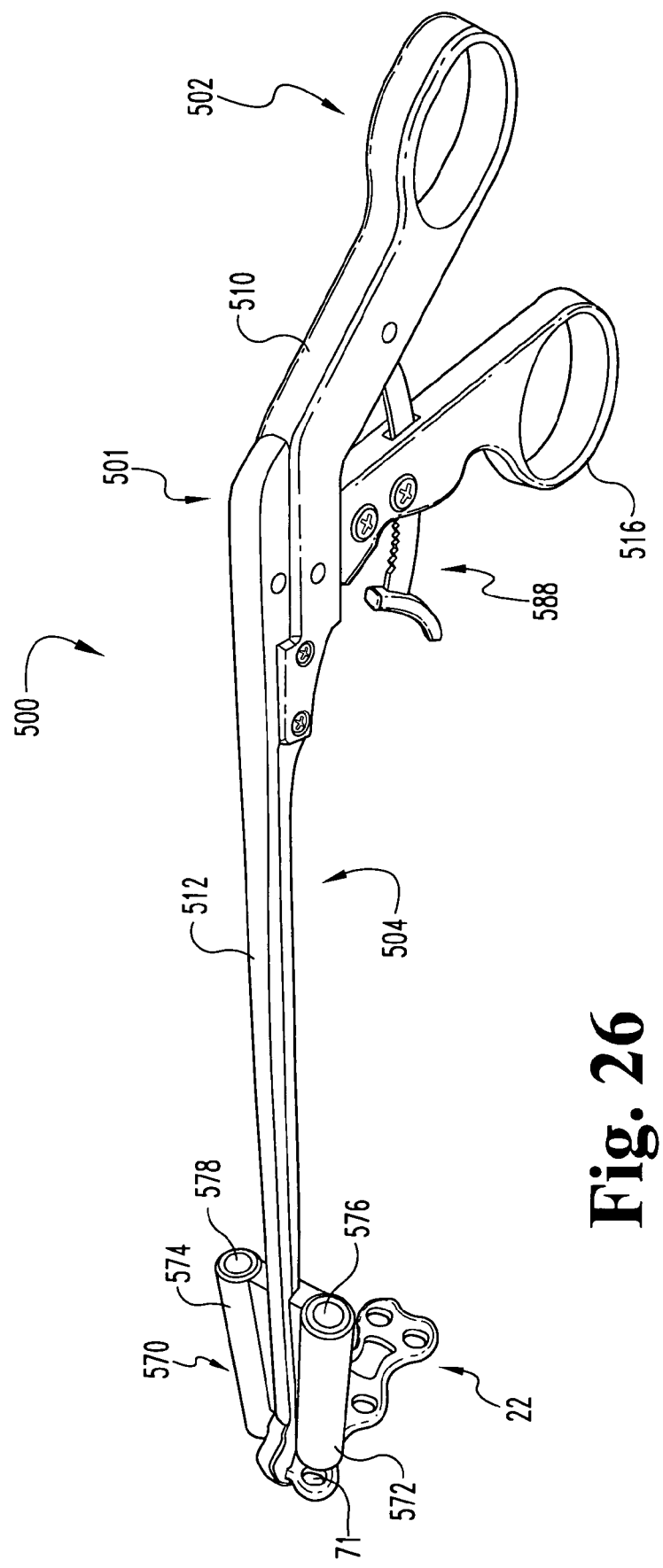
FIG. 26 is a perspective view of the holding instrument of FIG. 25 secured to a plate.

Referring now to FIGS. 25-27, another embodiment holding instrument includes a mechanism for facilitating the placement drills, taps, and or bone engaging fasteners through the plate holes in the desired angular orientation. Holding instrument 500 is the same as holding instrument 500 discussed above, except for the inclusion of guide mechanism 570 and the alteration of the orientation of the locking system. Locking system 588 includes a locking arm 589 having a ratchet surface 586 located along one side thereof like locking arm 562. However, the locking arm 589 is pivotally attached to first handle portion 510, and extends through a passage formed through second handle portion 516. Ratchet surface 586 is oriented upwardly along a concavely curved portion of the locking arm, and biased into engagement with one or more locking members (not shown) on second handle portion 516. A distally extending grasping portion 587 facilitates the surgeon in rotating the locking arm away from the locking member in second handle portion 516 when it is desired to release the plate or implant secured in holding system 506. An orientation such as that shown with locking system 508 can also be used.

A guide mechanism 570 can be permanently or releasably attached to connecting system 504 of holding instrument 500. As shown in FIG. 27, a coupling mechanism 577 can be attached to the stationary second member 513, and guide mechanism 570 can be attached, integrally formed, or otherwise secured to coupling mechanism 577. Guide mechanism 570 can be provided with one or more guide members 572, 574 including passages 576, 578 alignable with holes 70, 71, respectively, of plate 22. Passages 576, 578 are sized so that a bone engaging fastener can be positioned therethrough and guided to the proper location and orientation relative to plate 22, such as shown in FIG. 27.

Connecting system 504 and holding system 506 are positioned substantially in alignment with longitudinal axis 21 of plate 22 so that holes 70, 71 remain accessible by the surgeon through guide mechanism 570. Holding system 506 grips or holds plate 22 along end surfaces or end walls oriented transversely to longitudinal axis 21 of plate 22. The surgeon can visualize the holes from either side of guide mechanism 570, and also from the cephalad and caudal directions, without holding system 506 obstructing the surgeon's view.

As shown in FIG. 27, a bone engaging fastener 24, 25 can be positioned through hole 70, 71 of plate 22. A driving instrument 590 includes a shaft 592 slidably received in and guided by guide member 574 through passage 578 thereof. A tool engaging end 594 engages a tool recess in the head of fastener 24, 25. Fastener 24, 25 is positioned into hole 70, 71 along axis 72, 73 having an orientation with respect to plate 22 as discussed above. With holding system 506 engaged to plate 22, the central axis of passage 576, 578 is oriented in alignment with axis 72, 73.

In the illustrated embodiment, second holding member 540 is angled relative to proximal portion of second member 513 at an angle 543 so that with holding member 540 oriented substantially perpendicularly to plate 22 connecting system 504 extends caudally or away from the upper end surface of plate 22. This locates actuating system 501 out of the way of the surgeon so that guide mechanism 570 is unobstructed. In addition, guide mechanism 570 can be mounted on connecting system 504 so that the bone engaging fasteners are positioned along axis 72, 73 of holes 70, 71. Other embodiments contemplate guide mechanism 570 mounted to place fasteners along other axes relative to plate 22.

Guide mechanism 570 can be permanently attached to connector system 504, or releasably attached thereto for interchangeability with other guide mechanisms that provide different angular orientations or to accommodate other instrument sizes and/or types. It is further contemplated that holding instrument 500 can be provided without a guide mechanism, and the drilling, tapping and/or fastener insertion is completed through the plate holes via freehand techniques or other guiding instruments.

Guide mechanism 570 can be used to guide self-drilling screws, such as bone engaging fastener 700 discussed above, that are driven directly into the underlying vertebrae or bone. Guide mechanism 570 can also receive a sleeve, such as sleeve 595 in FIG. 25 to facilitate preparation of the hole to receive bone engaging fasteners that require pre-drilled and/ or pre-tapped holes. Sleeve 595 includes a distal portion 596 positionable through the passage of one or both of the guide members 572, 574, and a proximal portion 596 that abuts the proximal end of the respective guide member 572, 574 to secure sleeve 595 thereto. Sleeve 595 can include one or more fingers 598 extending from a distal end of proximal portion 597 that is positionable in a notch 573 opening toward the proximal end of the guide member, such as shown with respect to guide member 572. The interface between finger 598 and notch 573 prevents sleeve 595 from rotating relative to guide member 572. Sleeve 595 includes a central passage 599 extending therethrough sized to receive and guide a drilling instrument through guide member 572 and the plate holes into the underlying bone. Sleeve 595 can then be removed, and self-tapping screws can then be inserted into the drilled holes. Guide members 572, 574 can also be used with or without a sleeve to guide a tapping instrument into drilled holes, and screws then inserted into the drilled, tapped holes through the guide members. It is further contemplated that the bone engaging fasteners can be fixed or multi-axial relative to the plate.

Figure 28:
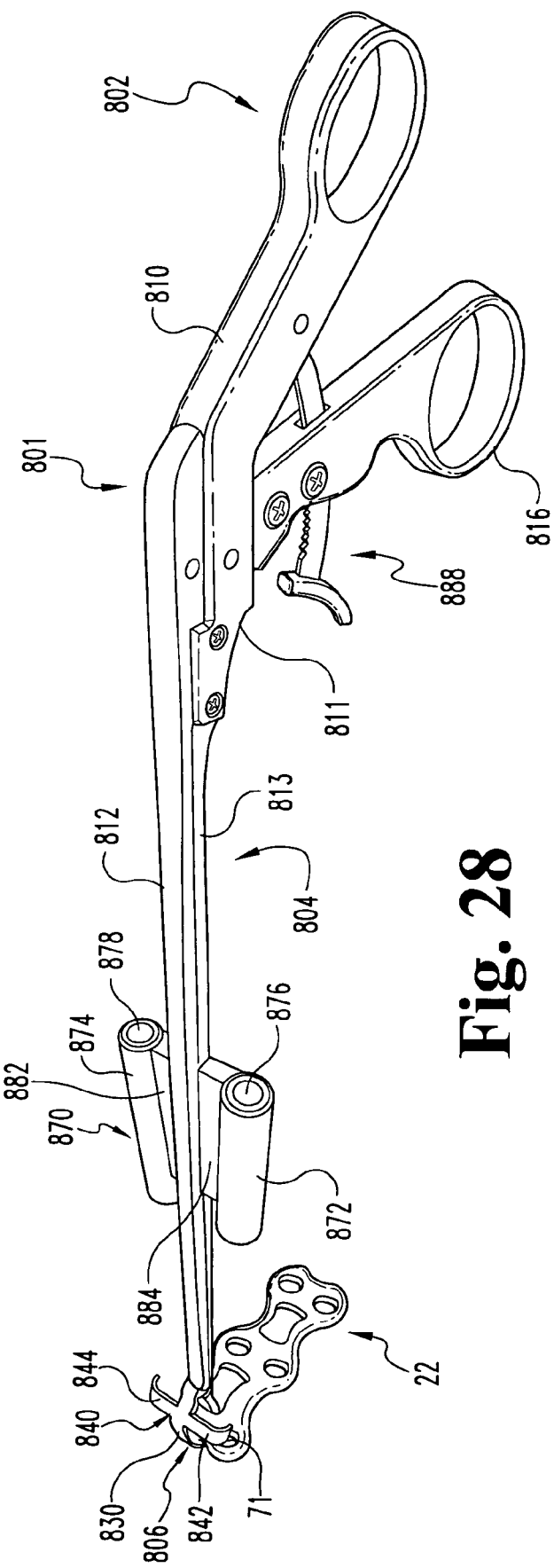
FIG. 28 is a perspective view of another embodiment holding instrument including a guide mechanism.
Figure 30:
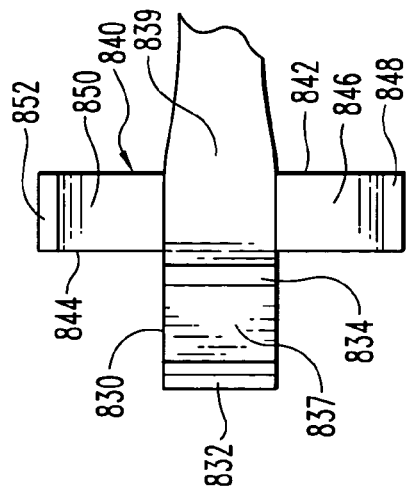
FIG. 30 is a bottom plan view of the distal portion of the holding instrument and guide mechanism of FIG. 28.
Figure 29:
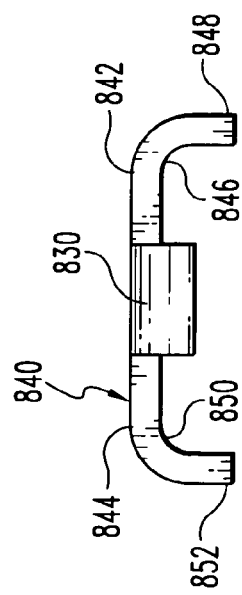
FIG. 29 is an end view of a distal portion of the holding instrument and guide mechanism of FIG. 28.

Referring now to FIGS. 28-30, another embodiment holding instrument includes a mechanism for facilitating the placement drills, taps, and or bone engaging fasteners through the plate holes in the desired angular orientation enhancing visualization of the placement. Holding instrument 800 can be similar to holding instrument 500 discussed above, except for the inclusion alignment mechanism 840 and the positioning of guide mechanism 870 relative thereto. Holding instrument 800 includes an actuating system 801 and a handle system 802. A connecting system 804 is operable with handle system 803 to move holding system 806 between a position engaged or clamped with the plate and a position released from the plate. Handle system 802 includes a first handle portion 810 and a second handle portion 816 pivotally secured to a frame portion 811 of first handle portion 810. Connecting system 804 includes a first member 812 coupled at its proximal end to frame portion 811 of first handle portion 810, and a second member 813 coupled at its proximal end to frame portion 811 of first handle portion 810. Locking system 888 can maintain the holding system 806 in a locked position with the plate engaged thereby.

Guide mechanism 870 can be permanently or releasably attached to connecting system 804 of holding instrument 800 with a coupling mechanism, such as coupling mechanism 577 in FIG. 27. The coupling mechanism can be attached to the stationary second member 813, and guide mechanism 870 can be attached, integrally formed, or otherwise secured with arms 882, 884 of the coupling mechanism. Guide mechanism 870 can be provided with one or more guide members 872, 874 including passages 876, 878 alignable with holes 70, 71, respectively, of plate 22. Passages 876, 878 are sized so that a driving instrument or guide sleeve can be positioned therethrough and guided along a desired orientation relative to plate 22.

Holding instrument 800 further includes an alignment mechanism 840 extending from holding system 806 that facilitates alignment of the distal end of the driving instrument, drilling instrument, and/or tapping instrument with the plate holes. Holding system 806 can be configured as discussed above with respect to holding system 506, and includes first and second holding members to firmly and releasably grip plate 22 therebetween. Alignment mechanism 840 permits guide mechanism 870 to be positioned proximally along connecting system 804 away from plate 22 so that the surgeon's view of the plate is further enhanced between alignment mechanism 840 and guide mechanism 870. Accordingly, a space between alignment mechanism 840 and guide mechanism 870 can be provided that only includes connecting system 804 with no devices or structures extending laterally therefrom that obstruct the surgeons vie of the plate holes during fastener placement.

Alignment mechanism 840 includes a first alignment member 842 extending laterally from first holding member 830 of holding system 806, and a second alignment member 844 extending laterally from first holding member 830 in a direction opposite first alignment member 842. Holding member 830 includes an engagement member 839 having a distal flange 832, a proximal flange 834, and a contacting surface 837 therebetween to receive the wall of the plate. First and second alignment members 842, 844 are offset proximally from proximal flange 834 for positioning along an upper surface of the plate 22 adjacent the respective plate holes 70, 71 when holding system 806 is engaged with the plate.

First alignment member 842 includes an arm with an end portion 848 curved toward the second holding member of holding system 806. An alignment surface 846 extends along alignment member 842, and is alignable with a side of the adjacent plate hole so that a driving instrument or the like positioned along alignment surface 846 is aligned with the center of the plate hole. Similarly, second alignment member 844 includes an arm with an end portion 852 curved toward the second holding member of holding system 806. An alignment surface 850 extends along alignment member 844, and is alignable with a side of the hole of the plate so that a driving instrument or the like positioned along alignment surface 850 is aligned with the center of the plate hole. The curved end portions 848, 852 resist lateral movement of the driving member relative to alignment mechanism 840. Alignment members 842, 844 are open along the side thereof oriented toward the second holding member to provide an unobstructed view of the holes 70, 71 of plate 22.

Connecting system 804 and holding system 806 are positioned substantially in alignment with longitudinal axis 21 of plate 22 so that holes 70, 71 remain accessible by the surgeon through guide mechanism 870 and alignment mechanism 840. Holding system 806 grips or holds plate 22 along end surfaces or end walls oriented transversely to longitudinal axis 21 of plate 22. Alignment members 842, 844 extend around a portion of holes 70, 71. With guide mechanism 870 offset along connecting system 804 away from plate 22, the open sides of alignment members 842, 844 permit the surgeon to visualize holes 70, 71 along a portion thereof opposite the portion occupied by alignment members 842, 844 without holding system 806 or alignment mechanism 840 obstructing the surgeon's view.

Any of the bone engaging fasteners 24, 25, 700 can be positioned through holes 70, 71 of plate 22 with a driving instrument slidably received in and guided by the respective guide member 872, 874 through passage 876, 878 thereof. Alignment mechanism 840 facilitates the surgeon maintaining the position of the distal end of the driving instrument relative to the plate while allowing visualization along the open side of the alignment members 842, 844. With holding system 806 engaged to plate 22, the central axes of passages 876, 878 and the alignment surfaces 846, 850 of alignment members 842, 844 are oriented relative to the plate to align the fastener and driving instrument with the corresponding hole axes 72, 73.

Guide mechanism 870 can be permanently attached to connector system 804, or releasably attached thereto for adjustment, interchangeability with other guide mechanisms, or for removal by the surgeon if desired. It is further contemplated that holding instrument 800 can be provided without a guide mechanism 870, and the drilling, tapping and/or fastener insertion is completed through the plate holes using alignment mechanism 840. Alignment members 842, 844 can be integrally formed with first holding member 830 as shown, or permanently or releasably attached thereto. Alignment mechanism 840 could alternatively be provided on the second holding member so that the alignment members open toward first holding member 830. It is further contemplated that alignment mechanism 840 can be provided with a single alignment member.

Guide mechanism 870 and alignment mechanism 840 can be used to guide self-drilling screws, such as bone engaging fastener 700, that are driven directly into the underlying vertebrae or bone. Guide mechanism 870 and alignment mechanism 840 can also receive a sleeve therethrough to guide a drilling instrument through the plate holes. Self-tapping screws can then be inserted into the drilled holes. Guide mechanism 870 and alignment mechanism 840 can also be used to guide a tapping instrument into drilled holes, and screws then inserted into the drilled, tapped holes through the guide members. It is further contemplated that the bone engaging fasteners can be fixed or multi-axial relative to the plate.

While the invention has been illustrated and described in detail in the drawings and foregoing description, the same is to be considered as illustrative and not restrictive in character, and that all changes and modifications that come within the spirit of the invention are desired to be protected.

The invention claimed is:

1. A spinal plating system, comprising:
an elongate plate including a length extending along a longitudinal axis adapted to span a space between adjacent vertebrae, said plate including a first connection portion attachable to a first one of the adjacent vertebrae and a second connection portion attachable to a second one of the adjacent vertebrae, and an intermediate portion extending between said first and second connection portions, said intermediate portion including a visualization opening extending therethrough for visualizing the space when said plate is attached to the adjacent vertebrae, said intermediate portion including a first member along one side of said visualization opening and a second member along the opposite side of said visualization opening, said first and second members each including a concavely curved outer side surface defining an outer most one of opposite sides of said plate and a concavely curved inner side surface opposite said respective outer side surface, said inner side surfaces defining respective ones of opposite sides of said visualization opening that extend along said longitudinal axis, wherein said first and second members each include a maximum width transversely to said longitudinal axis from said inner side surface to said outer side surface thereof that is uniform along a length of said visualization opening, said visualization opening including a minimum width transversely to said longitudinal axis between said opposite sides thereof, said minimum width of said visualization opening being greater than said maximum widths of said first and second members combined, wherein each of said connection portions includes a pair of openings each for receiving a bone anchor therethrough to attach said connection portion to the respective adjacent vertebrae, wherein each of said connection portions includes an aperture positioned between said pair of openings, wherein said aperture is sized and configured to receive a washer having a tapered portion configured to engage a surface of each said bone anchor positioned in each of said pair of openings, wherein a retaining device engageable to said plate locks said washer to said plate thereby fixedly securing said bone anchors in said pair of openings and preventing said pair of bone anchors from backing out of said plate.

2. The plating system of claim 1, wherein said visualization opening includes an hourglass shape.

3. The system of claim 1, wherein said first and second members are integrally formed with said first and second connection portions.

4. The system of claim 1, wherein said visualization opening includes end walls at opposite ends of said visualization opening, said end walls extending transversely to said longitudinal axis between said first and second members.

5. The system of claim 4, wherein said end walls are each concavely curved between said opposite sides of said visualization opening.

6. The system of claim 1, wherein said visualization opening is centered on said longitudinal axis of said plate.

7. The system of claim 1, further comprising a fusion member positionable in the space between adjacent vertebrae, said fusion member being visible through said visualization opening when said plate is attached to the adjacent vertebrae.

8. The system of claim 1, further comprising a holding instrument engage able to said plate, said holding instrument operable to apply a clamping force between an outer wall surface of said plate and a wall of said visualization opening adjacent said outer wall surface.

9. The system of claim 8, wherein said holding instrument includes a holding system including first and second holding members to apply said clamping force to said plate.

10. A spinal plating system, comprising:
an elongate plate extending along a longitudinal axis and including a length along the longitudinal axis adapted to span a space between adjacent vertebrae, said plate including a first connection portion attachable to a first one of the adjacent vertebrae and a second connection portion attachable to a second one of the adjacent vertebrae, and an intermediate portion extending between said first and second connection portions, wherein said first and second connection portions have substantially the same width across said longitudinal axis and each includes at least two holes on opposite sides of the longitudinal axis for receiving bone engaging fasteners, said intermediate portion including a visualization opening extending therethrough for visualizing the space when said plate is attached to the adjacent vertebrae, wherein said intermediate portion includes a first member along one side of said visualization opening and a second member along the opposite side of said visualization opening, said first and second members each including an outer side surface defining an outer most side of said plate and an inner side surface opposite said outer side surface, said inner side surfaces defining respective opposite sides of said visualization opening that extend along said longitudinal axis, wherein said first and second members each include a maximum width transversely to said longitudinal axis between said inner side and said outer side surface thereof, said visualization opening including a minimum width transversely to said longitudinal axis between said opposite sides thereof, said minimum width of said visualization opening being greater than said maximum widths of said first and second members combined, wherein said first and second connection portions include an aperture positioned between said at least two holes, said aperture sized and configured to receive a washer having a tapered portion configured to engage at least a portion of each of said bone engaging fasteners, wherein said washer is fixedly secured to said elongate plate with a retaining device received in said aperture thereby preventing said bone engaging fasteners from backing out of said plate.

11. The system of claim 10, wherein at least one of said sides of said visualization opening is convexly curved along the longitudinal axis.

12. The system of claim 11, wherein said outer side surfaces of said first and second members are concavely curved along the longitudinal axis adjacent said visualization opening.

13. The system of claim 10, wherein said minimum width is in the range from 100 percent to 125 percent of the combined maximum widths.

14. The system of claim 10, wherein said visualization opening includes a length along said longitudinal axis of said plate, said visualization opening including a length-to-width ratio ranging from 1.0 to 2.5.

15. The system of claim 10, wherein said visualization opening includes a length along said longitudinal axis of said plate, said visualization opening including a length-to-width ratio ranging from 1.0 to 1.5.

16. The system of claim 10, wherein said visualization opening includes a length along said longitudinal axis of said plate, said visualization opening including a length-to-width ratio ranging from 1.5 to 2.25.

17. The system of claim 10, wherein said visualization opening includes a length along said longitudinal axis of said plate, said visualization opening including a length-to-width ratio ranging from 1.0 to 2.0.

18. The system of claim 10, wherein said visualization opening includes opposite end walls extending transversely to said longitudinal axis between said opposite sides of said visualization opening.

19. The system of claim 18, wherein said opposite end walls are each concavely curved between said opposite sides of said visualization opening.

20. A system for stabilizing a portion of the spinal column, comprising:
a plate including a length extending along a longitudinal axis between a first connection portion for attachment to a first vertebra and a second connection portion for attachment to a second vertebra, said plate further including a visualization opening extending therethrough for visualizing a space between the first and second vertebrae, said plate further including a first outer end wall extending transversely to said longitudinal axis along said first connection portion and a second end wall extending transversely to said longitudinal axis in said visualization opening and adjacent to said first connection portion, said first and second connection portions including at least two holes spaced apart from said longitudinal axis for receiving bone engaging fasteners, said first and second connection portions further including an aperture along said longitudinal axis sized and configured to receive a washer having a tapered portion at least a portion of which being oriented to engage at least a portion of each of said bone engaging fasteners, said washer being secured in said aperture with a retaining device such that said washer prevents said bone engaging fasteners from backing out of said plate; and
a holding instrument including a remotely actuatable holding system engaged to said plate with a clamping force between said first and second end walls, wherein said holding system includes a first holding member and a second holding member engaged to respective ones of said first and second end walls to clamp said plate therebetween, wherein said first and second holding members move toward and away from one another in a direction that follows said longitudinal axis of said plate and further comprising a pair of guide members on said holding instrument positioned on opposite sides of said longitudinal axis when said holding system is engaged to said plate.

21. The system of claim 20, wherein said second end wall is concavely curved toward said first end wall across said longitudinal axis.

22. The system of claim 21, wherein said visualization opening includes at least one convexly surface side wall extending along said longitudinal axis of said plate.

23. The system of claim 20, wherein said holding system is adapted to hold said plate along said longitudinal axis of said plate.

24. The system of claim 20, wherein said holding instrument includes a proximal handle system and a connecting system operably connecting said holding system to said handle system, wherein said connecting system includes a stationary member and a linkage movable relative to said stationary member with said handle system to move said first holding member relative to said second holding member to engage said plate therebetween, said pair of guide members being mounted to said stationary member proximally of said holding system.

25. The system of claim 20, wherein said first end wall is concavely curved and said second end wall is concavely curved, said first holding member including a convexly curved plate contacting surface adapted to conform to the concavely curved first end wall and said second holding member including a convexly curved plate contacting surface adapted to conform to the concavely curved second end wall.

26. The system of claim 20, wherein said second holding member is fixed and said first holding member is pivotally attached to said second holding member and movable relative to said second holding member and said pair of guide members between a clamping position and a release position while said second holding member and said pair of guide members are stationary.

27. The system of claim 26, wherein said first holding member includes a proximal portion including a first end pivotally attached to said second holding member, said proximal portion extending transversely to said second holding member, said first holding member further including an intermediate portion extending from a second end of said proximal portion opposite said first end, said intermediate portion extending generally in the direction of said second holding member and forming a space with said second holding member to facilitate viewing of a portion of said plate clamped between said first and second holding members.

28. A spinal plating system, comprising:
a plate having a length extending along a longitudinal axis from a first connection portion for connection to a first vertebra to a second connection portion for connection to a second vertebra, said plate including a pair of bone engaging fastener holes positioned on opposite sides of said longitudinal axis and an aperture positioned between said pair of bone engaging holes along said longitudinal axis, said aperture sized and configured to receive a washer having a tapered portion and at least a portion of which is configured to engage at least a portion of each of said pair of bone engaging fasteners when positioned each of said pair of bone engaging fastener holes;
a holding instrument comprising:
an actuating system including a movable linkage member and a stationary member, wherein said linkage member moves relative to said second member upon actuation of said actuating system;
a holding system operably coupled to said actuating system, said holding system including first and second holding members coupled to respective ones of said linkage and said stationary member, wherein said first member is movable along said longitudinal axis with said actuating system between a release position and a clamping position with said second member to selectively engage and release said plate therebetween along said longitudinal axis thereof; and
a guide mechanism along said actuating system including at least one guide member offset from said longitudinal axis and mounted to said stationary member proximally of said holding system with said guide member spaced proximally from said plate when said holding system is engaged to said plate along said longitudinal axis and with said at least one guide member positioned relative to said plate to guide placement of said bone engaging fasteners through said pair of bone engaging fastener holes.

29. The system of claim 28, wherein
said guide mechanism includes a pair of guide members alignable with respective ones of said first and second bone engaging fastener holes, said first and second holding members being positioned between said pair of guide members.

30. The system of claim 28, wherein said holding instrument further comprises an alignment mechanism adjacent said holding system and distal of said guide mechanism, said alignment mechanism including at least one alignment member extending laterally from said holding system along said at least one bone engaging fastener hole of said plate.

31. A spinal plating system, comprising:
an elongate plate including a length extending along a longitudinal axis adapted to span a space between adjacent vertebrae, said plate including a first connection portion attachable to a first one of the adjacent vertebrae and a second connection portion attachable to a second one of the adjacent vertebrae, said first and second connection portions having substantially the same width across said longitudinal axis and an intermediate portion extending between said first and second connection portions, said first and second connection portions including at least two holes offset from said longitudinal axis for receiving a pair of bone engaging members, said first and second connection portions including an aperture between said at least two holes, said aperture sized and configured to receive a washer having a tapered portion, said tapered portion of said washer configured to engage each of said pair of bone engaging members to prevent said bone engaging members from backing out of said plate, wherein said intermediate portion is comprised of a translucent material for visualizing the space when said plate is attached to the adjacent vertebrae, said intermediate portion further comprising a visualization opening extending therethrough for visualizing the space when said plate is attached to the adjacent vertebrae, a first member along one side of said visualization opening and a second member along an opposite side of said visualization opening, said first and second members each including an outer side surface defining an outer most side of said plate and an inner side surface opposite said outer side surface, said inner side surfaces defining respective opposite sides of said visualization opening that extend along said longitudinal axis, wherein said first and second members each include a maximum width transversely to said longitudinal axis between said inner side and said outer side surface thereof, said visualization opening including a minimum width transversely to said longitudinal axis between said opposite sides thereof, said minimum width of said visualization opening being greater than said maximum widths of said first and second members combined.

32. The system of claim 31, wherein said first and second members each include a uniform width along said visualization opening between said outer side surface and said inner side surface thereof.

33. The system of claim 31, wherein said visualization opening includes at least one convexly curved side wall extending along the longitudinal axis and is further defined by upper and lower end walls having concave curvatures across said longitudinal axis.

34. The system of claim 31, wherein said entire plate is comprised of translucent material.

35. A spinal plating system, comprising:
an elongate plate including a length extending along a longitudinal axis adapted to span a space between adjacent vertebrae, said plate including a first connection portion attachable to a first one of the adjacent vertebrae and a second connection portion attachable to a second one of the adjacent vertebrae, and an intermediate portion extending between said first and second connection portions, said intermediate portion including a visualization opening extending therethrough for visualizing the space when said plate is attached to the adjacent vertebrae, wherein each of said connection portions includes a pair of openings each for receiving a bone anchor therethrough to attach said connection portion to the respective adjacent vertebrae, said first and second connection portions including an aperture between said pair of openings, said aperture sized and configured to receive a washer having a tapered portion at least a portion of which is configured to engage a portion of each of said bone anchors positioned in each of said pair of openings, each of said connection portions including a retaining device engage able to said aperture to fixedly secure said washer in said aperture and prevent said bone anchors in said pair of openings from backing out of said plate, wherein said intermediate portion includes a first member along one side of said visualization opening and a second member along an opposite side of said visualization opening, said first and second members each include a concavely curved outer surface extending along opposite outer edges of said plate between said first and second connection portions, said first and second members further including a convexly curved inner surface opposite said outer surface thereof, said inner surfaces extending along and defining respective sides of said visualization opening, wherein said inner and outer surfaces of said first member and said inner and outer surfaces of said second member each define a width along said longitudinal axis that is uniform along a length of said visualization opening.

36. The system of claim 35, wherein said visualization opening includes opposite end walls extending across the longitudinal axis and each of said end walls define said visualization opening with a concave curvature at the longitudinal axis.

37. The system of claim 35, wherein said visualization opening includes a minimum width between said convexly curved inner surfaces of said first and second members, said minimum width being greater than said uniform widths of said first and second members combined.

38. A spinal plating system, comprising:
a plate extending along a longitudinal axis, said plate including a first connection portion attachable to a first one of the adjacent vertebrae and a second connection portion attachable to a second one of the adjacent vertebrae and an intermediate portion extending between said first and second connection portions, said first and second connection portions having a pair of bone engaging fastener holes offset to one side of said longitudinal axis sized and configured to receive a pair of bone engaging fasteners, said first and second connection portions having an aperture between said pair of bone engaging fastener holes, said aperture sized and configured to receive a washer having a tapered portion configured to engage at least a portion of each of said pair of bone engaging fasteners, said intermediate portion defining a visualization window with an upper end adjacent said first connection portion and lower end adjacent said second connection portion, said upper and lower ends having substantially the same width across said longitudinal axis;
a holding instrument comprising:
an actuating system including a movable linkage member and a stationary member, wherein said linkage member moves relative to said stationary member upon actuation of said actuating system;
a holding system operably coupled to said actuating system, said holding system including first and second holding members movable with said actuating system between a release position and a clamping position to selectively engage and release said plate therebetween along said longitudinal axis thereof; and
a guide mechanism along said actuating system including at least one guide member mounted to said stationary member proximally to said holding system and in offset relation to said longitudinal axis so that said at least one guide member is positioned relative to said plate to guide placement of said bone engaging fasteners through said pair of holes when said first and second holding members are engaged to said plate along said longitudinal axis.

39. The system of claim 38, wherein
said guide mechanism includes a pair of guide members alignable with respective ones of said first and second bone engaging fastener holes, said first and second holding members being positioned between said pair of guide members.

40. The system of claim 38, wherein said holding instrument further comprises an alignment mechanism adjacent said holding system and distal of said guide mechanism, said alignment mechanism including at least one alignment member extending laterally from said holding system along said at least one bone engaging fastener hole of said plate.

* * * * *

UNITED STATES PATENT AND TRADEMARK OFFICE
CERTIFICATE OF CORRECTION

| | |
|---|---|
| PATENT NO. | : 7,862,597 B2 |
| APPLICATION NO. | : 10/603471 |
| DATED | : January 4, 2011 |
| INVENTOR(S) | : Gause et al. |

It is certified that error appears in the above-identified patent and that said Letters Patent is hereby corrected as shown below:

In Column 7, Line 3, delete "7 1" and insert -- 71 --, therefor.

In Column 21, Line 22, in Claim 8, delete "engage able" and insert -- engageable --, therefor.

In Column 25, Line 44, in Claim 35, delete "engage able" and insert -- engageable --, therefor.

Signed and Sealed this
Twenty-sixth Day of April, 2011

David J. Kappos
*Director of the United States Patent and Trademark Office*